United States Patent
Kubodera et al.

[11] Patent Number: 5,824,811
[45] Date of Patent: Oct. 20, 1998

[54] 22-THIAVITAMIN $D_3$ DERIVATIVES

[75] Inventors: Noboru Kubodera; Akira Kawase, both of Shizuoka-ken, Japan

[73] Assignee: Chugai Seiyaku Kabushiki Kaisha, Tokyo, Japan

[21] Appl. No.: 718,499

[22] PCT Filed: Apr. 10, 1995

[86] PCT No.: PCT/JP95/00699

§ 371 Date: Oct. 1, 1996

§ 102(e) Date: Oct. 1, 1996

[87] PCT Pub. No.: WO95/27697

PCT Pub. Date: Oct. 19, 1995

[30] Foreign Application Priority Data

Apr. 11, 1994 [JP] Japan ................................ 6-107336

[51] Int. Cl.$^6$ .......................... C07C 401/00; C07J 13/00; C07J 5/00
[52] U.S. Cl. .......................... 552/653; 552/533; 552/560; 552/582; 574/167
[58] Field of Search ................................ 552/653, 533, 552/560, 582; 514/167

[56] References Cited

U.S. PATENT DOCUMENTS 5,554,599  9/1996  Gue-Sorensen et al. ................ 514/167

FOREIGN PATENT DOCUMENTS 42 20 757 A    5/1994   Germany .
91 15475      10/1991   WIPO .
9414766        7/1994   WIPO .......................... C07C 401/00

OTHER PUBLICATIONS

E. Murayama, K. Miyamoto, N. Kubodera, T. Mori, and I. Matsunaga, "Synthesis of 22–Oxavitamin $D_3$ Analogues" Chemical Pharm. Bull., 34 (10) 4410–4413 (1986).

N. Kobodera, K. Miyamoto, M. Akiyama, M. Matsumoto, and T. Mori Synthetic Studies of Vitamin D Analogues. IX[1].) 1a,25–Dihydroxy–23–ox–, thia–, and azavitamin $D_3$[2]) Chemical. Pharm. Bull., 39 (12) 3221–3224 (1991).

N. Kobodera, H. Watanabe, T. Kawanishi, and M. Matsumoto, Synthetic Studies of Vitamin D Analogues. XI.[1]) 1a,25–Dihydroxy–22–oxavitamin $D_3$ Analogues Chemical Pharm. Bull., 40 (6) 1494–1499 (1992).

Kawase, et al. Bioorg & Med Chem Lett, 5(3), pp. 279–280, 2 Feb. 1995.

Primary Examiner—Allen J. Robinson
Assistant Examiner—Barbara Badio
Attorney, Agent, or Firm—Browdy and Neimark

[57] ABSTRACT

Compounds of the general formula:

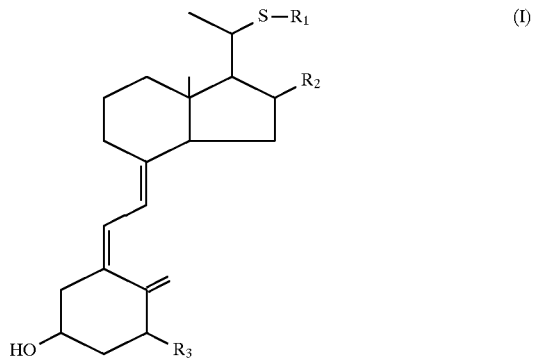

wherein $R_1$ represents a C1-10 alkyl group which may be substituted by one or more hydroxyl groups, $R_2$ represents a hydrogen atom or a hydroxyl group, and $R_3$ represents a hydrogen atom or a hydroxyl group; their intermediates; as well as synthesis processes of these compounds and intermediates are disclosed. The compounds of this invention, vitamin D derivatives substituted by sulfur atoms at the 22-position have a strong inhibitory effect against proliferation of keratinocytes.

40 Claims, 3 Drawing Sheets

22-THIAVITAMIN D₃ DERIVATIVES

This application is a 371 of PCT/JP95/00699 filed Apr. 10, 1995.

1. Field of the Invention

This invention relates to novel vitamin $D_3$ derivatives. More specifically, this invention relates to vitamin $D_3$ derivatives substituted by sulfur atoms at the 22-position and processes for preparing said derivatives. This invention also relates to intermediates which are useful for preparing said compounds and processes for preparing said intermediates.

2. Description of the Prior Art

Active-type vitamin $D_3$ is known to have many physiological activities including calcium metabolism regulation, differentiation induction, immunoregulation, etc.

In recent years, physiological activities of D vitamins have been gradually illuminated. D vitamins, such as 1α,25-dihydroxyvitamin $D_3$, are known to exhibit a wide range of physiological activities including calcium metabolism regulation, proliferation inhibition or differentiation induction of oncocytes or the like, immunoregulation, etc. However, 1α,25-dihydroxyvitamin $D_3$ is not suitable for use as, for example, antineoplastic, antirheumatic, etc., because it disadvantageously causes hypercalcemia after long-term and continuous administration. Thus, a number of vitamin D derivatives have recently been synthetized in order to divide these activities of D vitamins, and their physiological activities have been investigated.

One example of such derivatives is 1α,3β-dihydroxy-20 (S)-(3-hydroxy-3-methylbutyloxy-9,10-secopregna-5,7,10 (19)-triene which is a derivative of vitamin $D_3$ substituted by an oxygen atom at the 22-position, disclosed in JPA (Unexamined Japanese Patent Application) 61-267550 (1986).

DISCLOSURE OF THE INVENTION

After profound study on vitamin D derivatives, the inventors of this invention found that vitamin D derivatives substituted by sulfur atoms at the 22-position have a strong inhibitory effect against proliferation of keratinocytes.

This invention relates to 22-thiavitamin D derivatives of the following general formula (I):

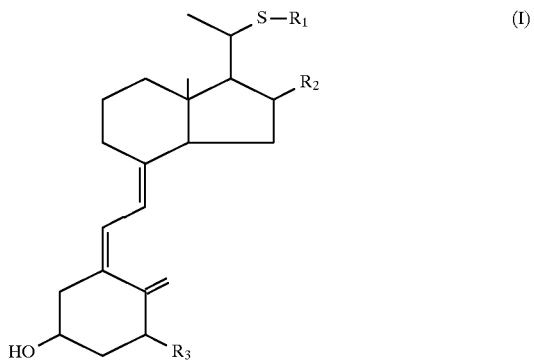

wherein $R_1$ represents a C1-10 alkyl group which may be substituted by one or more hydroxyl groups, $R_2$ represents a hydrogen atom or a hydroxyl group, and $R_3$ represents a hydrogen atom or a hydroxyl group; and processes for preparing said derivatives.

This invention also relates to synthetic intermediates which are useful for preparing the compounds of the general formula (I) and processes for preparing said intermediates.

THE BEST EMBODIMENTS OF THE INVENTION

Figure 1:
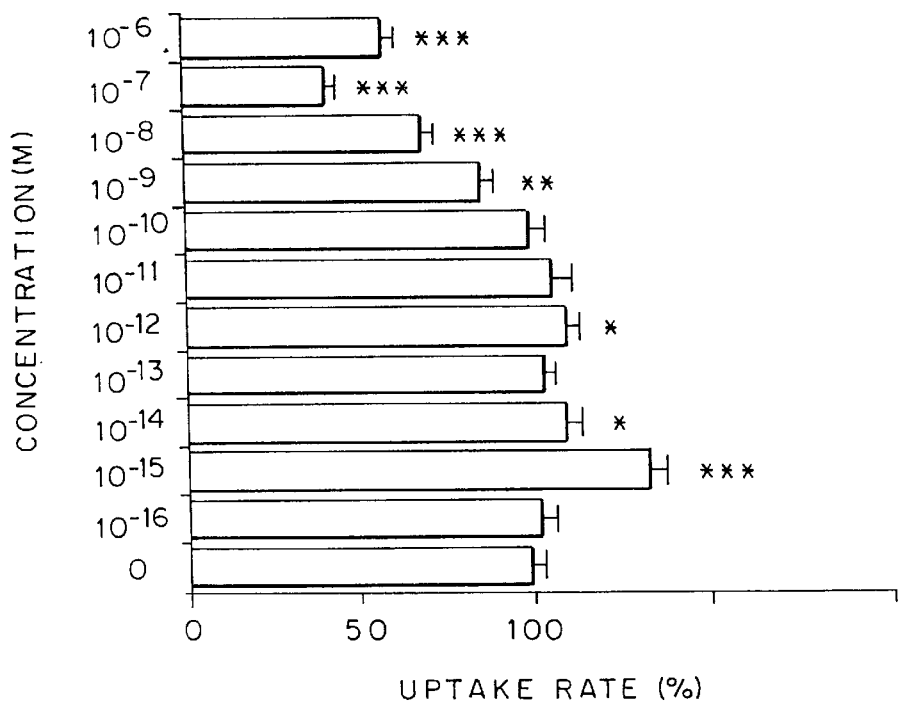
FIG. 1 is a graph showing an inhibitory effect against proliferation of human keratinocytes at each concentration of 1α,25-dihydroxyvitamin $D_3$.

As described above, this invention provides 22-thiavitamin D derivatives of the following general formula (I):

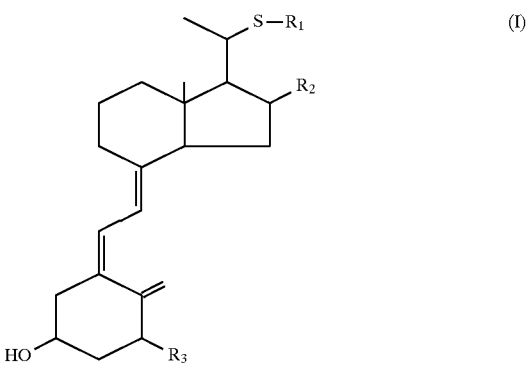

wherein $R_1$ represents a C1-10 alkyl group which may be substituted by one or more hydroxyl groups, $R_2$ represents a hydrogen atom or a hydroxyl group, and $R_3$ represents a hydrogen atom or a hydroxyl group.

In the compounds of the general formula (I), $R_3$ is preferably a hydroxyl group. $R_1$ is preferably a C1-10 alkyl group substituted by one or more hydroxyl groups, and more preferably a group of the following general formula (III):

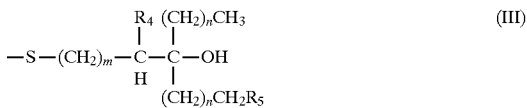

wherein $R_4$ and $R_5$, which may be the same or different, each represents a hydrogen atom or a hydroxyl group provided that the both are not hydroxyl groups, m represents an integer of 1 through 4, and n represents an integer of 0 through 2. More preferably, $R_4$ and $R_5$ are hydrogen atoms.

The steric configuration of the general formula (I) is not specifically limited, but preferably corresponds the general formula (II):

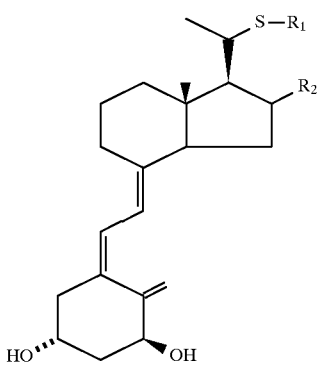

(II)

wherein $R_1$ represents a C1-10 alkyl group which may be substituted by one or more hydroxyl groups, and $R_2$ represents a hydrogen atom or a hydroxyl group.

This invention also relates to processes for preparing vitamin $D_3$ derivatives substituted by sulfur atoms at the 22-position. Accordingly, this invention relates to a process for preparing a compound of the general formula (XVI):

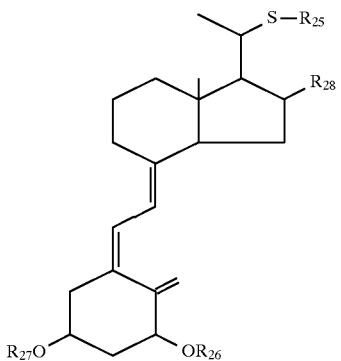

(XVI)

wherein $R_{25}$ represents a C1-10 alkyl group which may be substituted by one or more hydroxyl groups, $R_{26}$ and $R_{27}$, which may be the same or different, each represents a hydrogen atom or a protective group, and $R_{28}$ represents a hydrogen atom or a hydroxyl group, by subjecting a compound of the general formula (XV):

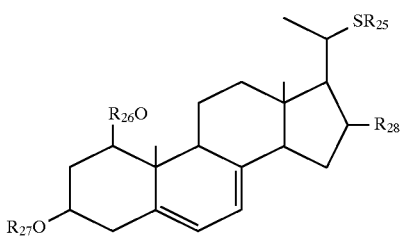

(XV)

wherein $R_{25}$ represents a C1-10 alkyl group which may be substituted by one or more hydroxyl groups, $R_{26}$ and $R_{27}$, which may be the same or different, each represents a hydrogen atom or a protective group, and $R_{28}$ represents a hydrogen atom or a hydroxyl group, to a light irradiation and thermal isomerization reaction.

This invention also provides synthetic intermediates which are useful for preparing the compounds of the general formula (I) and processes for preparing said intermediates.

Representative examples of the synthetic intermediates include, for example, compounds of the general formula (VI):

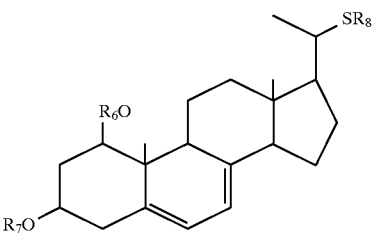

(VI)

wherein $R_6$ and $R_7$, which may be the same or different, each represents a hydrogen atom or a protective group, and $R_8$ represents a C1-10 alkyl group which may be substituted;

compounds of the general formula (XI):

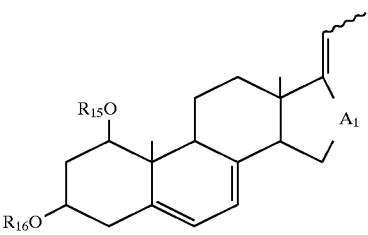

(XI)

wherein $R_{15}$ and $R_{16}$, which may be the same or different, each represents a hydrogen atom or a protective group, and $A_1$ represents —CHOH— or —CO—; and compounds of the general formula (XIII):

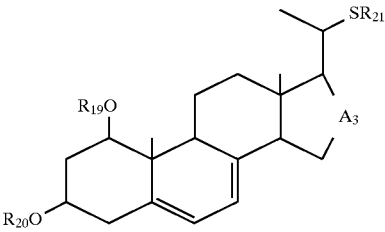

(XIII)

wherein $R_{19}$ and $R_{20}$, which may be the same or different, each represents a hydrogen atom or a protective group, $R_{21}$ represents a C1-10 alkyl group which may be substituted, and $A_3$ represents —CHOH— or —CO—.

Especially preferred examples of the synthetic intermediates include, for example, compounds of the general formula (X):

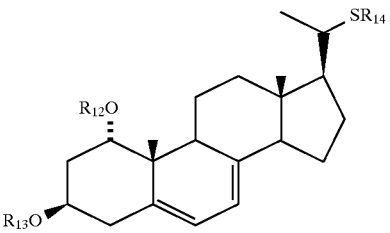

(X)

wherein $R_{12}$ and $R_{13}$, which may be the same or different, each represents a hydrogen atom or a protective group, and $R_{14}$ represents a C1-10 alkyl group which may be substituted;

compounds of the general formula (XII):

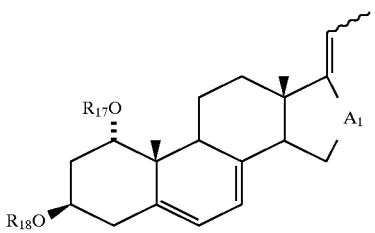

(XII)

wherein $R_{17}$ and $R_{18}$, which may be the same or different, each represents a hydrogen atom or a protective group, and $A_2$ represents —CHOH— or —CO—; and compounds of the general formula (XIV):

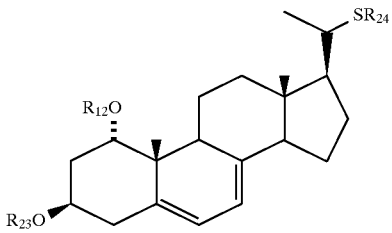

(XIV)

wherein $R_{22}$ and $R_{23}$, which may be the same or different, each represents a hydrogen atom or a protective group, $R_{24}$ represents a C1-10 alkyl group which may be substituted, and $A_4$ represents —CHOH— or —CO—.

Each of $R_8$, $R_{11}$, $R_{14}$, $R_{21}$ and $R_{24}$ is preferably a C1-10 alkyl group substituted by one or more hydroxyl groups, more preferably a group of the general formula (III):

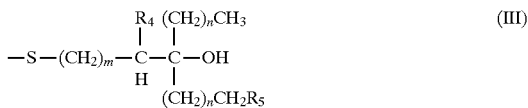

(III)

wherein $R_4$ and $R_5$, which may be the same or different, each represents a hydrogen atom or a hydroxyl group provided that the both are not hydroxyl groups, m is an integer of 1 through 4 and n is an integer of 0 through 2, and most preferably a group of the general formula (III) wherein $R_4$ and $R_5$ are hydrogen atoms.

For the purpose of this invention, the C1-10 alkyl group which may be substituted by hydroxyl groups represents a straight or branched chain alkyl group such as methyl, ethyl, n-propyl, i-propyl, n-butyl, i-butyl, s-butyl, t-butyl, pentyl, hexyl, heptyl, octyl, nonyl and decanyl groups. Preferable examples are 3-methylbutyl, 3-ethylpentyl, 4-methylpentyl, 3-(n-propyl)hexyl, 4-ethylhexyl, 5-methylhexyl, 6-methylheptyl, 5-ethylheptyl and 4-(n-propyl)heptyl groups, more preferably 3-methylbutyl, 3-ethylpentyl and 4-methylpentyl groups.

In the C1-10 alkyl which may be substituted by one or more hydroxyl groups, the number of hydroxyl substituents is for example, 0, 1, 2, 3, preferably 1 or 2, more preferably 1.

Examples of the C1-10 alkyl group substituted by one or more hydroxyl groups include 3-hydroxy-3-methylbutyl, 2-hydroxy-3-methylbutyl, 4-hydroxy-3-methylbutyl, 2,3-dihydroxy-3-methylbutyl, 2,4-dihydroxy-3-methylbutyl, 3,4-dihydroxy-3-methylbutyl, 3-hydroxy-3-ethylpentyl, 2-hydroxy-3-ethylpentyl, 4-hydroxy-3-ethylpentyl, 2,3-dihydroxy-3-ethylpentyl, 2,4-dihydroxy-3-ethylpentyl, 3,4-dihydroxy-3-ethylpentyl, 4-hydroxy-4-methylpentyl, 3-hydroxy-4-methylpentyl, 5-hydroxy-4-methylpentyl, 3,4-dihydroxy-4-methylpentyl, 3,5-dihydroxy-4-methylpentyl, 4,5-dihydroxy-4-methylpentyl, 3-hydroxy-3-(n-propyl) hexyl, 4-hydroxy-3-(n-propyl)hexyl, 2-hydroxy-3-(n-propyl)hexyl, 2,3-dihydroxy-3-(n-propyl)hexyl, 3,4-dihydroxy-3-(n-propyl)hexyl, 2,4-dihydroxy-3-(n-propyl) hexyl, 3-hydroxy-4-ethylhexyl, 4-hydroxy-4-ethylhexyl, 5-hydroxy-4-ethylhexyl, 3,4-dihydroxy-4-ethylhexyl, 3,5-dihydroxy-4-ethylhexyl, 4,5-dihydroxy-4-ethylhexyl, 4-hydroxy-5-methylhexyl, 5-hydroxy-5-methylhexyl, 6-hydroxy-5-methylhexyl, 4,5-dihydroxy-5-methylhexyl, 4,6-dihydroxy-5-methylhexyl, 5,6-dihydroxy-5-methylhexyl, 5-hydroxy-6-methylheptyl, 6-hydroxy-6-methylheptyl, 7-hydroxy-6-methylheptyl, 5,6-dihydroxy-6-methylheptyl, 5,7-dihydroxy-6-methylheptyl, 6,7-dihydroxy-6-methylheptyl, 4-hydroxy-5-ethylheptyl, 5-hydroxy-5-ethylheptyl, 6-hydroxy-5-ethylheptyl, 4,5-dihydroxy-5-ethylheptyl, 4,6-dihydroxy-5-ethylheptyl, 5,6-dihydroxy-5-ethylheptyl, 3-hydroxy-4-(n-propyl)heptyl, 4-hydroxy-4-(n-propyl)heptyl, 5-hydroxy-4-(n-propyl) heptyl, 3,4-dihydroxy-4-(n-propyl)heptyl, 3,5-dihydroxy-4-(n-propyl)heptyl and 4,5-dihydroxy-4-(n-propyl)heptyl groups, preferably 3-hydroxy-3-methylbutyl, 2,3-dihydroxy-3-methylbutyl, 3,4-dihydroxy-3-methylbutyl, 3-hydroxy-3-ethylpentyl, 2,3-dihydroxy-3-ethylpentyl, 3,4-dihydroxy-3-ethylpentyl, 4-hydroxy-4-methylpentyl, 3,4-dihydroxy-4-methylpentyl and 4,5-dihydroxy-4-methylpentyl groups, more preferably 3-hydroxy-3-methylbutyl, 3-hydroxy-3-ethylpentyl and 4-hydroxy-4-methylpentyl groups.

The protective group in this invention includes acyl, substituted silyl, substituted alkyl groups or the like, preferably acyl and substituted silyl groups.

The acyl group in this invention means a formyl group, a lower alkylcarbonyl group which may be substituted, an arylcarbonyl group which may be substituted, an aralkylcarbonyl group which may be substituted, a lower alkyloxycarbonyl group which may be substituted, an aryloxycarbonyl group which may be substituted or an aralkyloxycarbonyl group which may be substituted, preferably a formyl group, a lower alkylcarbonyl group, a phenylcarbonyl group which may be substituted, a lower alkyloxycarbonyl group, a phenylalkyloxycarbonyl group which may be substituted, more preferably formyl, acetyl, propionyl, butyryl, pivaloyl, benzoyl, ethoxycarbonyl, t-butoxycarbonyl, benzyloxycarbonyl groups.

The substituted silyl group means a silyl group which is substituted by one or more lower alkyl groups which may be substituted or aryl groups which may be substituted, etc., preferably a tri-substituted silyl group. Preferable examples of the substituted silyl group include trimethylsilyl, triethylsilyl, triisopropylsilyl, t-butyldiphenylsilyl and t-butyldimethylsilyl groups.

The substituted alkyl group means an alkyl group substituted by one or more substituents. Preferable examples of the substituent are an aryl group which may be substituted, an alkyloxy group which may be substituted, etc., especially an alkyloxy group which may be substituted by an alkyloxy or other group. The alkyloxy group which may be substituted by an alkyloxy or other group includes, for example, methoxymethyl, 2-methoxyethoxymethyl and tetrahydropyran-2-yl groups.

The protective group for each of $R_6$, $R_7$, $R_{12}$, $R_{13}$ is preferably stable under acidic conditions, more preferably an acyl group, most preferably an acetyl group. The protective group for each of $R_9$, $R_{10}$, $R_{15}$, $R_{16}$, $R_{17}$, $R_{18}$, $R_{19}$, $R_{20}$, $R_{22}$, $R_{23}$ is preferably a substituted silyl group, more preferably trimethylsilyl, triethylsilyl, triisopropylsilyl, t-butyldimethylsilyl and t-butyldiphenylsilyl groups, more preferably t-butyldimethylsilyl group.

The reducing conditions in this invention mean that a reducing agent exists in the reaction system, said reducing agent including borane, trialkylsilane, preferably trialkylsilane, more preferably triethylsilane.

The basic conditions in this invention mean that a base which may form a thioalcoholate exists in the reaction system, said base including potassium hydroxide, sodium hydroxide, sodium tetraborate, preferably sodium tetraborate.

The substituents in this invention include, for example, a halogen atom, and cyano, nitro, hydroxyl, alkoxy, amino, mercapto and acyloxy groups.

Especially preferable examples of the substituents in $R_8$, $R_{11}$, $R_{14}$, $R_{21}$, $R_{24}$ are, for example, hydroxyl, alkoxy and acyloxy groups, most preferably a hydroxyl group.

The compounds of this invention have a strong inhibitory effect against proliferation of keratinocytes. In the compounds of this invention, the steric configuration at the 20-position and the steric configuration of hydroxyl groups may be either R or S, or either α or β.

The compounds of this invention are preferably substituted at the 1-position by a hydroxyl group which is preferably in α-configuration.

All the compounds of this invention are novel and synthesized as described below, for example.

The thiol which is used as a starting material for synthesis of side chains from the 22-position was synthesized by the process described in JPA-5-505613 (1993) or the process of the following Scheme 1:

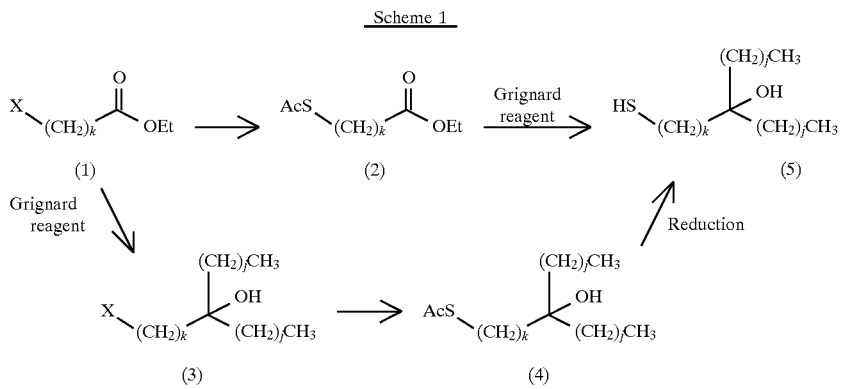

wherein X represents a halogen atom, j represents an integer of 0 through 2 and k represents an integer of 2 through 5.

Namely, it is obtained by starting with a halogenated ester and reacting it with 1) a metal salt of a thiocarboxylic acid such as potassium thioacetate, and 2) a Grignard reagent. It may also be obtained by reacting the starting material with 2) at first and then 1), and hydrolyzing thus obtained compound under reducing or alkali conditions.

The compounds of the general formula (I) wherein $R_2$ represents a hydrogen atom are synthesized by the process of the following Scheme 2, for example:

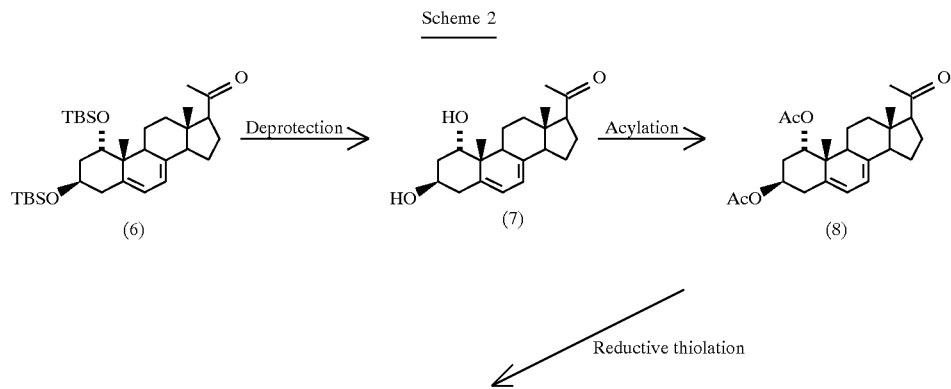

-continued
Scheme 2

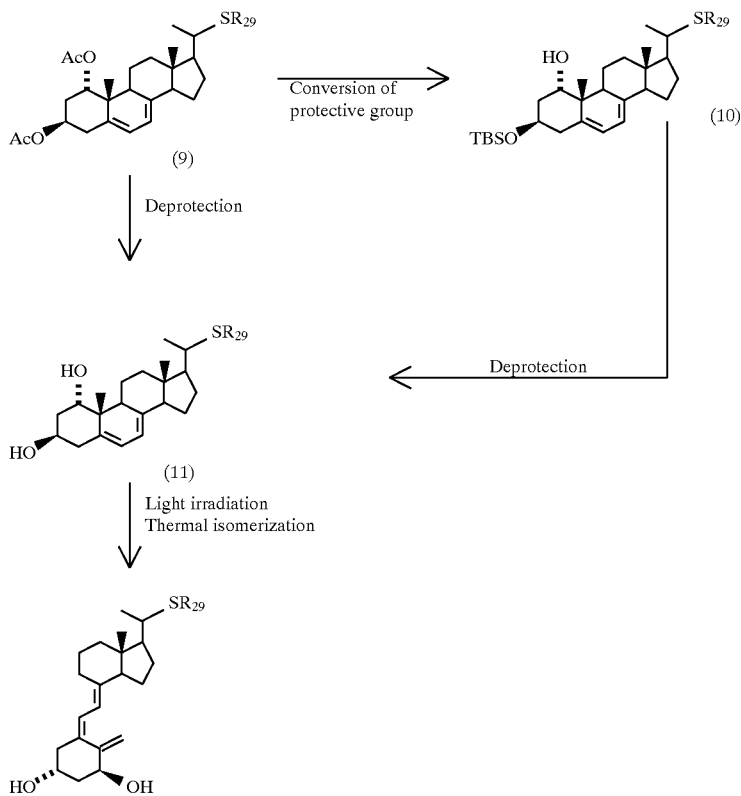

wherein $R_{29}$ represents a C1-10 alkyl group which may be substituted.

In Scheme 2, the starting compound (6) is synthesized by, for example, the process of Murayama et al. (Bioorg. Med. Chem. Lett. 2, 1289 (1992)). The hydroxyl group of this compound (6) is deprotected and thereafter reprotected by an acyl group, preferably an acetyl group, to give the compound (8). This compound (8) is subjected to a reductive thiolation reaction to give the compound (9). The reductive thiolation is carried out, for example, by using boron trifluoride-ether complex or boron trifluoride monohydrate/ triethylsilane, or trifluoroacetic acid/borane-pyridine complex, preferably by using boron trifluoride-ether complex/triethylsilane.

The solvent used in this reaction includes, for example, halogenous solvents, ethereal solvents, aromatic hydrocarbonaceous solvents, preferably halogenous solvents, more preferably, dichloromethane.

The reaction temperature depends on the nature of the compound used, the reagent and other factors, but generally corresponds to a temperature at which 5,7-diene moiety is not isomerized, preferably between $-30°$ C. and room temperature, more preferably around $0°$ C.

The reaction time depends on the reagent used, the amount of the compound and other factors, but generally ranges from 1 to 12 hours, preferably 3 to 10 hours, more preferably 5 to 7 hours.

Then, the compound (9) obtained as above is deprotected in a conventional manner, and optionally after separation of diastereomers, subjected to a light irradiation and thermal isomerization reaction to give the compound (12). If it is difficult to separate diastereomers in this step, the protective group of the hydroxyl group at either one or the both of the 1- and 3-positions may be converted into an appropriate protective group according to the necessity to allow them to be separated.

The compounds of the general formula (I) wherein $R_2$ represents a hydroxyl group are synthesized by, for example, the process of the following Scheme 3:

Scheme 3

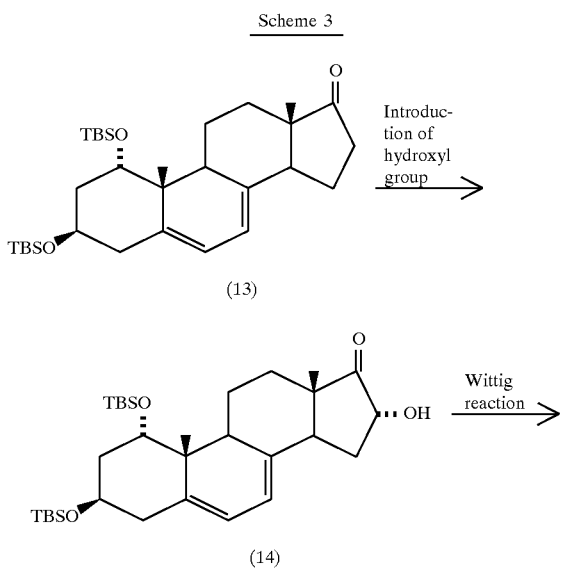

-continued
Scheme 3

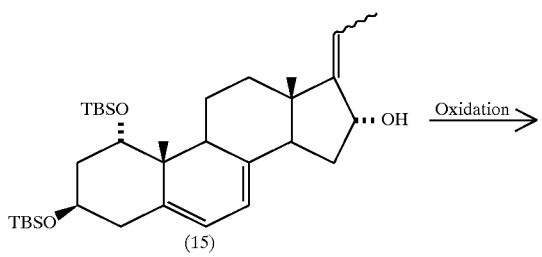

Scheme 5

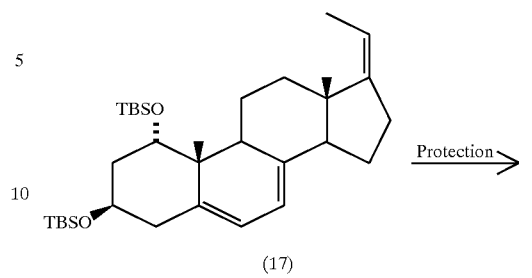

In Scheme 3, the starting compound (13) is synthesized by, for example, the process of Murayama et al. (Chem. Pharm. Bull. 34, 4410 (1986)). At first, an oxygen functional group is introduced into the 16-position of the compound (13). The oxygen functional group is introduced by, for example, using 2-(phenylsulfonyl)-3-phenyloxazylidine in the presence of a base, or introducing a halogen into the 16-position and then converting it into a hydroxyl group, preferably by using 2-(phenylsulfonyl)-3-phenyloxazylidine in the presence of a base. The base used here includes metal alkoxides, metal amides, metal hydrides, etc., preferably metal alkoxides, more preferably potassium t-butoxide.

The compound (14) obtained as above is subjected to a Wittig-type reaction to give the compound (15) consisting of an E, Z mixture, which is then converted into the compound (16) by oxidation reaction. This reaction may be an ordinary oxidation reaction using chromate, dimethyl sulfoxide, etc., preferably an oxidation reaction using dimethyl sulfoxide. If the E, Z mixture of the compound (15) is oxidized by manganese dioxide in this step, only the reaction of the E-isomer proceeds to yield the compound (16) consisting of the E-isomer. The unreacted Z-isomer of the compound (15) can be stereoselectively led to the compound (16) consisting of the Z-isomer by Swern oxidation or the like as shown in the following Scheme 4.

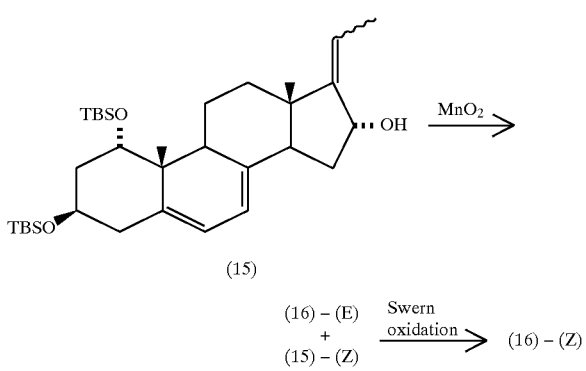

The E-isomer of the compound (15) can also be synthesized by the process of the following Scheme 5.

The starting compound (17) in Scheme 5 can be synthesized by, for example, the process of Murayama et al. (Chem. Pharm. Bull. 34, 4410 (1986)). The 5,7-diene moiety of the compound (17) is protected by a protective group such as 4-phenyl-1,2,4-triazoline-3,5-dione, thereafter oxidized by an oxidizing agent such as selenium dioxide, chromic acid, manganese (III) acetate, preferably selenium dioxide, and deprotected to give the E-isomer of the compound (15).

The compound (16) obtained by the process described above is converted into the compound (20) by 1,4-addition of various thiols as shown in the following Scheme 6:

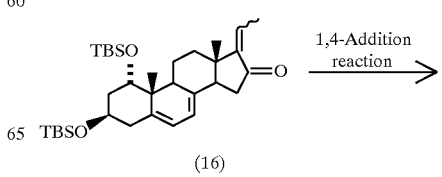

-continued
Scheme 6

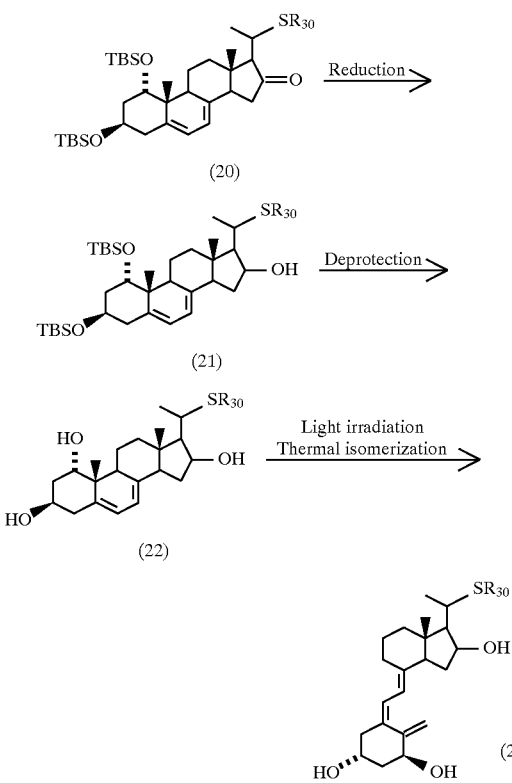

wherein $R_{30}$ represents a C1-10 alkyl group which may be substituted.

This reaction can be effected by applying an ordinary 1,4-addition reaction for α,β-unsaturated ketones. This reaction may be carried out, for example, under basic conditions, preferably by using sodium hydroxide, sodium tetraborate, more preferably sodium tetraborate.

The solvent used here depends on the reagent used and other factors. When sodium tetraborate is used, the solvent is an ethereal or alcoholic solvent used alone or as mixture with water, preferably a mixed solvent of an ethereal solvent and water, more preferably a mixed solvent of tetrahydrofuran and water.

The reaction temperature depends on the reagent used and other factors, but generally ranges from −20° to 60° C., preferably 0° to 40° C., more preferably 15° to 25° C.

The reaction time depends on the reagent used, the amount of the compound and other factors, but generally ranges from 3 to 24 hours, preferably 9 to 15 hours, more preferably 12 to 15 hours.

The compound (20) obtained as above can be converted into the compound (23) through reduction, deprotection, light irradiation and thermal isomerization in a conventional manner.

The following examples further explain this invention in detail, but are not intended to limit the scope of this invention.

EXAMPLE 1

4-Ethyl-4-hydroxy-1-hexanethiol

To acetone (30 ml) were added 4-bromobutyric acid ethyl ester (1.5 ml, 10.5 mmol) and potassium thioacetate (1.8 g, 15.8 mmol), and the mixture was stirred at room temperature for 30 minutes and then filtered, and the solids were washed with acetone. The filtrate was concentrated, and then purified by column chromatography on silica gel (hexane:ethyl acetate=5:1) to give 4-acetylthiobutyric acid ethyl ester (2.03 g). Then, ethyl magnesium bromide (1.04M solution in tetrahydrofuran, 31.3 ml, 32.6 mmol) in dry tetrahydrofuran (8 ml) was cooled to 0° C. under an argon atmosphere, and a solution of 886 mg of the compound obtained as above in dry tetrahydrofuran (4 ml) was added dropwise and the mixture was stirred at room temperature for 2 hours. The reaction mixture was quenched with an aqueous saturated ammonium chloride solution, acidified with 10% hydrochloric acid and extracted with ethyl acetate. The extract was washed with brine and dried over magnesium sulfate. The solvent was distilled off under reduced pressure and the residue was purified by column chromatography on silica gel (hexane:ethyl acetate=4:1) to give the title compound (221 mg, 2 steps, 29%).

IR(neat): 3450, 2950, 2550, 1460, 1370, 1240, 1170 cm$^{-1}$.

$^1$H NMR(60 MHz) δ: 2.47(t,2H), 1.74–1.08(m,8H), 0.84 (t,6H).

EXAMPLE 2

5-Hydroxy-5-methyl-1-hexanethiol

Under an argon atmosphere, to a solution of methyl magnesium bromide (0.99M solution in tetrahydrofuran, 70 ml, 69.3 mmol) in dry tetrahydrofuran (80 ml) was added a solution of ethyl 5-bromovalerate (3.66 ml, 23.1 mmol) in dry tetrahydrofuran (10 ml) dropwise at 0° C., and the mixture was stirred at room temperature for 1.5 hour, then quenched with an aqueous saturated ammonium chloride solution, poured into water and extracted with ethyl acetate. The extract was washed with brine and dried over magnesium sulfate. The solvent was distilled off under reduced pressure to give crude 6-bromo-2-methyl-2-hexanol (5.28 g). This crude product was dissolved into acetone (80 ml) and potassium thioacetate (3.96 g, 34.7 mmol) was added. The mixture was stirred at room temperature for 1.5 hour and filtered, then the filtrate was concentrated under reduced pressure. The residue was purified by column chromatography on silica gel (hexane:ethyl acetate: 4:1) to give 6-acetylthio-2-methyl-2-hexanol (3.75 g). Thus obtained 6-acetylthio-2-methyl-2-hexanol was dissolved into tetrahydrofuran (130 ml) and lithium aluminum hydride (2.24 g, 59.0 mmol) was added by portions at 0° C. After this suspension was stirred at room temperature for 1.5 hour, excessive lithium aluminium hydride was treated with ethyl acetate and the reaction solution was acidified with 4N hydrochloric acid. The solution was extracted with ethyl acetate, and the organic layer was washed with brine, dried over magnesium sulfate, then the solvent was removed under reduced pressure. The residue was purified by column chromatography on silica gel (hexane:ethyl acetate=4:1) to give the title compound (2.95 g, 3 steps, 85%).

IR(neat): 3400, 2950, 2550, 1460, 1370, 1240, 1140, 1040 cm$^{-1}$.

$^1$H NMR(60 MHz) δ: 2.47(t,2H), 1.92–1.28(m,6H), 1.18 (s,6H).

EXAMPLE 3

6-Hydroxy-6-methyl-1-heptanethiol

The title compound was synthesized from ethyl 6-bromocaproate by the same procedure as in Example 2.

IR(neat): 3400, 2950, 2550, 1460, 1370, 1240, 1140, 1040 cm$^{-1}$.

$^1$H NMR(60 MHz) δ: 2.47(t,2H), 1.92–1.28(m,8H), 1.18 (s,6H).

EXAMPLE 4

3-Hydroxy-3-n-propyl-1-hexanethiol

The title compound was synthesized from ethyl 3-bromopropionate and n-propyl magnesium bromide by the same procedure as in Example 2.

IR(neat): 3450, 2950, 2550, 1460, 1370, 1240, 1150, 1040 cm$^{-1}$.

$^1$H NMR(60 MHz) δ: 2.47(t,2H), 1.94–0.74(m,16H).

EXAMPLE 5

1α,3β-Dihydroxy-20-oxopregna-5,7-diene

Under an argon atmosphere, to a solution of 1α,3β-bis(t-butyldimethylsilyloxy)-20-oxopregna-5,7-diene (4.10 g, 7.33 mmol) in dry tetrahydrofuran (80 ml), was added tetra-n-butylammonium fluoride (1M solution in tetrahydrofuran, 74 ml, 74.0 mmol), and the mixture was refluxed for 16 hours. Then the mixture was poured into water and extracted with ethyl acetate. The organic layer was washed successively with 10% hydrochloric acid, an aqueous saturated sodium bicarbonate solution and brine, and dried over magnesium sulfate. After the solvent was distilled off under reduced pressure, the residue was purified by column chromatography on silica gel (dichloromethane:ethanol=15:1) to give the title compound (1.68 g, 69%) as a white solid.

IR(neat): 3400, 2930, 1700, 1360, 1050 cm$^{-1}$.

$^1$H NMRδ: 5.73–5.66(m,1H), 5.43–5.36(m,1H), 4.12–3.93(m,1H), 3.80–3.73(brs,1H), 2.16(s,3H), 0.93(s,3H), 0.59(s,3H).

MS m/z: 330(M$^+$), 251(100%).

UV λ$_{max}$ nm: 271, 283, 294.

EXAMPLE 6

1α,3β-Diacetoxy-20-oxopregna-5,7-diene

A solution of the compound obtained in Example 5 (1.68 g, 5.08 mmol), acetic anhydride (30 ml) and 4-dimethylaminopyridine (DMAP, 60 mg) in pyridine (60 ml) was stirred at room temperature for 4 days. The reaction mixture was poured into water and extracted with ethyl acetate. The organic layer was washed with brine and dried over magnesium sulfate. The solvent was distilled off under reduced pressure and the residue was purified by column chromatography on silica gel (hexane:ethyl acetate=3:1) to give the title compound (1.65 g, 78%) as a white solid.

IR(neat): 2970, 1740, 1700, 1440, 1360, 1240, 1040 cm$^{-1}$.

$^1$H NMRδ: 5.70–5.60(m,1H), 5.44–5.34(m,1H), 5.07–4.85(m,2H), 2.14(s,3H), 2.10(s,3H), 2.04(s,3H), 1.01(s,3H), 0.57(s,3H).

MS m/z: 414(M$^+$), 294(100%).

UV λ$_{max}$ nm: 270, 281, 292.

EXAMPLE 7

1α,3β-Diacetoxy-20-(3-hydroxy-3-methylbutylthio) pregna-5,7-diene (mixture of 20R- and S-isomers)

Under an argon atmosphere, a solution of the compound obtained in Example 6 (100 mg, 0.241 mmol) and 3-methyl-3-hydroxy-1-butanethiol (34.7 mg, 0.289 mmol) in dry dichloromethane (0.5 ml) was cooled to 0° C. and stirred with boron trifluoride-ether complex (35.5 μl, 0.289 mmol) for 3 minutes, then stirred with triethylsilane (57.8 μl, 0.362 mmol) at 0° C. for 5.5 hours. Then the reaction mixture was poured into water and extracted with ethyl acetate. The organic layer was washed with an aqueous saturated sodium bicarbonate solution and brine and dried over magnesium sulfate, then the solvent was removed under reduced pressure. The residue was purified by preparative thin-layer chromatography (2 plates, dichloromethane:ethanol=20:1, developed once) to give the title compound mixture (55.7 mg, 45%) as a colorless oil. The starting material (43.3 mg, 35%) was also recovered.

IR(neat): 3460, 2960, 1740, 1370, 1240, 1030 cm$^{-1}$.

$^1$H NMRδ: 5.70–5.60(m,1H), 5.42–5.32(m,1H), 5.07–4.84(m,2H), 2.09(s,3H), 2.03(s,3H), 1.39 and 1.30(d of each diastereomer, J=6.3 and 6.6 Hz, 3H), 1.25(s,6H), 1.01(s,3H), 0.69 and 0.65(s of each diastereomer, 3H).

MS m/z: 518(M$^+$), 69(100%).

UV λ$_{max}$ nm: 273, 282, 293.

EXAMPLE 8

1α,3β-Diacetoxy-20(S)-(4-ethyl-4-hydroxyhexylthio)pregna-5,7-diene and 1α,3β-diacetoxy-20(R)-(4-ethyl-4-hydroxyhexylthio) pregna-5,7-diene After the procedure of Example 7 was followed using the compound obtained in Example 6 (150 mg, 0.361 mmol), the compound obtained in Example 1 (73.0 mg, 0.450 mmol), boron trifluoride-ether complex (55.3 μl, 0.450 mmol), dry dichloromethane (1 ml) and triethylsilane (201 μl, 1.26 mmol), the residue was purified by preparative thin-layer chromatography (4 plates, dichloromethane:ethyl acetate=9:1, developed once) to give a mixture of the title compounds (38.8 mg, 19%) as a colorless oil as well as a recovered material 1α,3β-diacetoxy-20-oxopregna-5,7-diene (89.4 mg). Thus obtained mixture was further purified by preparative thin-layer chromatography (4 plates, dichloromethane:ethyl acetate=25:1, developed 5 times) to give the title compounds 20S-isomer (8.6 mg, 4%) and 20R-isomer (21.1 mg, 10%) both as colorless oils.

20S-isomer:

IR(neat): 3500, 2950, 1740, 1460, 1370, 1240, 1030 cm$^{-1}$.

$^1$H NMRδ: 5.69–5.63(m,1H), 5.42–5.35(m,1H), 5.04–4.88(m,2H), 2.09(s,3H), 2.04(s,3H), 1.46(q,J=7.3 Hz,4H), 1.38(d,J=6.3 Hz,3H), 1.01(s,3H), 0.86(t,J=7.3 Hz,6H), 0.65(s,3H).

MS m/z: 560(M$^+$), 143(100%).

UV λ$_{max}$ nm: 270, 281, 293.

20R-isomer:

IR(neat): 3500, 2950, 1740, 1460, 1370, 1240, 1050 cm$^{-1}$.

$^1$H NMRδ: 5.69–5.61(m,1H), 5.40–5.31(m,1H), 5.06–4.97(m,2H), 2.08(s,3H), 2.04(s,3H), 1.49(q,J=7.3 Hz,4H), 1.29(d,J=6.6 Hz,3H), 1.01(s,3H), 0.86(t,J=7.3 Hz,6H), 0.69(s,3H).

MS m/z: 560(M$^+$), 143(100%).

UV λ$_{max}$ nm: 270, 281, 293.

EXAMPLE 9

1α,3β-Diacetoxy-20-(4-hydroxy-4-methylpentylthio)pregna-5,7-diene (mixture of 20R- and S-isomers)

After the procedure of Example 7 was followed using the compound obtained in Example 6 (200 mg, 0.482 mmol), 4-hydroxy-4-methylpentanethiol (77.6 mg, 0.578 mmol), boron trifluoride-ether complex (71.0 µl, 0.578 mmol), dry dichloromethane (1 ml) and triethylsilane (115 µl, 0.723 mmol), the residue was purified by preparative thin-layer chromatography (4 plates, hexane:ethyl acetate=1:1, developed once) to give a mixture of the title compounds (93.3 mg, 36%) as a colorless oil as well as a recovered material (133 mg).

IR(neat): 3450, 2950, 1740, 1371, 1240, 1030 cm$^{-1}$.

$^1$H NMR δ: 5.70–5.60(m,1H), 5.42–5.32(m,1H), 5.07–4.84(m,2H), 2.54(t,J=7.3 Hz,2H), 2.09(s,3H), 2.03(s,3H), 1.39 and 1.29(d of each diastereomer, J=7.3 and 6.6 Hz,3H), 1.23(s,6H), 1.01(s,3H), 0.69 and 0.65(s of each diastereomer, 3H).

MS m/z: 532(M$^+$), 55(100%).

UV $\lambda_{max}$ nm: 270, 282, 293.

EXAMPLE 10

1α,3β-Diacetoxy-20(S)-(3-ethyl-3-hydroxypentylthio)pregna-5,7-diene and 1α,3β-diacetoxy-20(R)-(3-ethyl-3-hydroxypentylthio)pregna-5,7-diene After the procedure of Example 7 was followed using the compound obtained in Example 6 (180 mg, 0.434 mmol), 3-ethyl-3-hydroxypentanethiol (85.7 mg, 0.578 mmol), boron trifluoride-ether complex (71.0 µl, 0.578 mmol), dry dichloromethane (1 ml) and triethylsilane (115 µl, 0.723 mmol), the residue was purified by preparative thin-layer chromatography (4 plates, dichloromethane:ethyl acetate=9:1, developed once) to give a mixture of the title compounds as a colorless oil as well as a recovered material (50.1 mg). Thus obtained mixture was further purified by preparative thin-layer chromatography (4 plates, dichloromethane:ethyl acetate=30:1, developed 5 times) to give the title compounds 20S-isomer (12.5 mg, 5%) and 20R-isomer (28.2 mg, 12%) both as colorless oils.

20S-isomer:

IR(neat): 3500, 2950, 1740, 1460, 1370, 1240, 1030 cm$^{-1}$.

$^1$H NMR δ: 5.68–5.60(m,1H), 5.40–5.31(m,1H), 5.07–4.85(m,2H), 2.59(t,J=7.8 Hz,2H), 2.09(s,3H), 2.04(s,3H), 1.49(q,J=7.3 Hz,4H), 1.40(d,J=6.6 Hz,3H), 1.01(s,3H), 0.87(t,J=7.3 Hz,6H), 0.65(s,3H).

MS m/z: 546(M$^+$), 55(100%).

UV $\lambda_{max}$ nm: 270, 281, 293

20R-isomer:

IR(neat): 3500, 2950, 1740, 1460, 1370, 1240, 1030 cm$^{-1}$.

$^1$H NMR δ: 5.70–5.60(m,1H), 5.41–5.30(m,1H), 5.05–4.84(m,2H), 2.56(t,J=8.2 Hz,2H), 2.08(s,3H), 2.03(s,3H), 1.49(q,J=7.3 Hz,4H), 1.30(d,J=6.6 Hz,3H), 1.01(s,3H), 0.87(t,J=7.3 Hz,6H), 0.69(s,3H).

MS m/z: 546(M$^+$), 55(100%).

UV $\lambda_{max}$ nm: 270, 281, 293.

EXAMPLE 11

1α,3β-Diacetoxy-20(S)-(5-hydroxy-5-methylhexylthio)pregna-5,7-diene and 1α,3β-diacetoxy-20(R)-(5-hydroxy-5-methylhexylthio)pregna-5,7-diene After the procedure of Example 7 was followed using the compound obtained in Example 6 (200 mg, 0.482 mmol), the compound obtained in Example 2 (85.7 mg, 0.578 mmol), boron trifluoride-ether complex (71.0 µl, 0.578 mmol), dry dichloromethane (1 ml) and triethylsilane (115 µl, 0.723 mmol), the residue was purified by preparative thin-layer chromatography (4 plates, dichloromethane:ethyl acetate=10:1, developed 3 times) to give the title compounds S-isomer (10.6 mg, 4%) and R-isomer (37.8 mg, 14%) both as colorless oils.

20S-isomer:

IR(neat): 3500, 2950, 1740, 1460, 1370, 1240, 1030 cm$^{-1}$.

$^1$H NMR δ: 5.71–5.63(m,1H), 5.43–5.35(m,1H), 5.07–4.88(m,2H), 2.09(s,3H), 2.04(s,3H), 1.38(d,J=6.3 Hz,3H), 1.22(s,6H), 1.01(s,3H), 0.65(s,3H).

MS m/z: 546(M$^+$), 278(100%).

UV $\lambda_{max}$ nm: 270, 281, 293.

20R-isomer:

IR(neat): 3500, 2950, 1740, 1460, 1370, 1240, 1030 cm$^{-1}$.

$^1$H NMR δ: 5.71–5.64(m,1H), 5.43–5.34(m,1H), 5.08–4.88(m,2H), 2.08(s,3H), 2.03(s,3H), 1.29(d,J=6.6 Hz,3H), 1.22(s,6H), 1.01(s,3H), 0.69(s,3H).

MS m/z: 546(M$^+$), 278(100%).

UV $\lambda_{max}$ nm: 270, 281, 293.

EXAMPLE 12

1α,3β-Diacetoxy-20(S)-(6-hydroxy-6-methylheptylthio)pregna-5,7-diene and 1α,3β-diacetoxy-20(R)-(6-hydroxy-6-methylheptylthio)pregna-5,7-diene After the procedure of Example 7 was followed using the compound obtained in Example 6 (200 mg, 0.482 mmol), the compound obtained in Example 3 (93.8 mg, 0.578 mmol), boron trifluoride-ether complex (71.0 µl, 0.578 mmol), dry dichloromethane (1 ml) and triethylsilane (115 µl, 0.723 mmol), the residue was purified by preparative thin-layer chromatography (4 plates, dichloromethane:ethyl acetate=7:1, developed once) to give a mixture of the title compounds and the starting thiol as a colorless oil as well as a recovered material (109 mg). Thus obtained mixture was further purified by preparative thin-layer chromatography (4 plates, dichloromethane:ethyl acetate 12:1, developed 5 times) to give a mixture of the title compound 20S-isomer and the starting thiol (33.9 mg) as well as the title compound 20R-isomer (26.4 mg, 10%) (both as colorless oils). The former was used in the subsequent reaction in this mixture state.

20R-isomer:

IR(neat): 3500, 2950, 1740, 1460, 1370, 1240, 1030 cm$^{-1}$.

$^1$H NMR δ: 5.71–5.62(m,1H), 5.40–5.32(m,1H), 5.07–4.86(m,2H), 2.08(s,3H), 2.03(s,3H), 1.28(d,J=6.8 Hz,3H), 1.21(s,6H), 1.01(s,3H), 0.69(s,3H).

MS m/z: 560(M$^+$), 278(100%).

UV $\lambda_{max}$ nm: 270, 281, 293.

EXAMPLE 13

1α,3β-Diacetoxy-20(S)-(3-hydroxy-3-n-propylhexylthio)pregna-5,7-diene and 1α,3β-diacetoxy-20(R)-(3-hydroxy-3-n-propylhexylthio)pregna-5,7-diene After the procedure of Example 7 was followed using the compound obtained in Example 6 (200 mg, 0.482 mmol), the compound obtained in Example 4 (102 mg, 0.578 mmol), boron trifluoride-ether complex (71.0 µl, 0.578 mmol), dry dichloromethane (1 ml) and triethylsilane (115 µl, 0.723 mmol), the residue was purified by preparative thin-layer chromatography (4 plates, hexane:ethyl acetate:ethanol=4:1:0.1, developed once) to give a mixture of the title compounds as a colorless oil (134 mg, 48%) as well as a recovered material (48.1 mg). Thus obtained mixture was further purified by preparative thin-layer chromatography (4 plates, dichloromethane:ethyl acetate=30:1, developed 4 times) to give the title compounds 20S-isomer (23.6 mg, 9%) and 20R-isomer (78.2 mg, 28%) both as colorless oils.

20S-isomer:
IR(neat): 3500, 2950, 1740, 1460, 1370, 1240, 1030 cm$^{-1}$.
$^1$H NMRδ: 5.71–5.61(m,1H), 5.44–5.32(m,1H), 5.08–4.87(m,2H), 2.57(t,J=7.8 Hz,2H), 2.09(s,3H), 2.03(s,3H), 1.01(s,3H), 0.92(t,J=6.8 Hz,6H), 0.65(s,3H).
MS m/z: 574(M$^+$), 157(100%).
UV $\lambda_{max}$ nm: 270, 281, 293.

20R-isomer:
IR(neat): 3500, 2950, 1740, 1460, 1370, 1240, 1030 cm$^{-1}$.
$^1$H NMRδ: 5.72–5.63(m,1H), 5.44–5.33(m,1H), 5.07–4.90(m,2H), 2.54(t,J=7.8 Hz,2H), 2.08(s,3H), 2.03(s,3H), 1.01(s,3H), 0.92(t,J=6.6 Hz,6H), 0.69(s,3H).
MS m/z: 574(M$^+$), 157(100%).
UV $\lambda_{max}$ nm: 270, 281, 293.

EXAMPLE 14

1α-Hydroxy-3β-(t-butyldimethylsilyloxy)-20(S)-(4-hydroxy-4-methylpentylthio)pregna-5,7-diene and 1α-hydroxy-3β-(t-butyldimethylsilyloxy)-20(R)-(4-hydroxy-4-methylpentylthio)pregna-5,7-diene Under an argon atmosphere, to a solution of the compound obtained in Example 9 (mixture) (93.3 mg, 0.175 mmol) in dry tetrahydrofuran (4 ml) was added lithium aluminum hydride (13.3 mg, 0.350 mmol) by portions. The mixture was stirred at room temperature for 30 minutes, then quenched with a 10% aqueous sodium hydroxide solution and extracted with ethyl acetate. The extract was washed with brine and dried over magnesium sulfate and the solvent was removed under reduced pressure. The residue was purified by preparative thin-layer chromatography (2 plates, dichloromethane:ethanol=17:3, developed once) to give 40.1 mg of colorless solids. Under an argon atmosphere, the solids were dissolved into dimethyl formamide (2.6 ml) and stirred with t-butyldimethylsilyl chloride (72.5 mg, 0.481 mmol) and imidazole (65.6 mg, 0.962 mmol) at room temperature for 2 hours. Then the reaction mixture was poured into water and extracted with hexane:ethyl acetate= 3:1. The organic layer was washed with brine, dried over magnesium sulfate, and the solvent was removed under reduced pressure. The residue was purified by preparative thin-layer chromatography (2 plates, hexane:ethyl acetate= 5:1, developed 6 times) to give the title compounds 20S-isomer (12.9 mg, 13%) and 20R-isomer (23.7 mg, 24%) both as colorless oils.

20S-isomer:
IR(neat): 3450, 2950, 1460, 1380, 1260, 1090 cm$^{-1}$.
$^1$H NMRδ: 5.73–5.64(m,1H), 5.41–5.31(m,1H), 4.11–3.91(m,1H), 3.72(brs,1H), 1.40(d,J=6.6 Hz,3H), 1.22(s,6H), 0.94(s,3H), 0.89(s,9H), 0.66(s,3H), 0.08(s,6H).
MS m/z: 562(M$^+$), 73(100%).
UV $\lambda_{max}$ nm: 271, 282, 294.

20R-isomer:
IR(neat): 3450, 2950, 1460, 1380, 1260, 1090 cm$^{-1}$.
$^1$H NMRδ: 5.72–5.63(m,1H), 5.38–5.29(m,1H), 4.12–3.92(m,1H), 3.72(brs,1H), 1.23(d,J=6.6 Hz,3H), 1.22(s,6H), 0.94(s,3H), 0.88(s,9H), 0.71(s,3H), 0.08(s,6H).
MS m/z: 562(M$^+$), 73(100%).
UV $\lambda_{max}$ nm: 271, 282, 294.

EXAMPLE 15

1α,3β-Dihydroxy-20(S)-(3-hydroxy-3-methylbutylthio)pregna-5,7-diene and 1α,3β-dihydroxy-20(R)-(3-hydroxy-3-methylbutylthio)pregna-5,7-diene Under an argon atmosphere, to a solution of the compound obtained in Example 7 (mixture) (55.0 mg, 0.106 mmol) in dry tetrahydrofuran (2 ml) was added lithium aluminum hydride (8.0 mg, 0.212 mmol) by portions, and the mixture was stirred at room temperature for 30 minutes. The reaction solution was quenched with a 10% aqueous sodium hydroxide solution and extracted with ethyl acetate. The organic layer was washed with brine, dried over magnesium sulfate, and the solvent was removed under reduced pressure. The residue was purified by preparative thin-layer chromatography (1 plate, dichloromethane:ethanol=17:1, developed 8 times) to give the title compounds 20S-isomer (10.1 mg, 22%) and 20R-isomer (19.3 mg, 42%) both as colorless oils.

20S-isomer:
IR(neat): 3400, 2950, 1460, 1380, 1050 cm$^{-1}$.
$^1$H NMRδ: 5.72–5.64(m,1H), 5.39–5.29(m,1H), 4.23–3.92(m,1H), 3.76(brs,1H), 2.64(t,J=7.9 Hz,2H), 1.41(d,J=6.6 Hz,3H), 1.25(s,6H), 0.95(s,3H), 0.67(s,3H).
MS m/z: 434(M$^+$), 69(100%).
UV $\lambda_{max}$ nm: 272, 282, 293.

20R-isomer:
IR(neat): 3400, 2950, 1460, 1380, 1050 cm$^{-1}$.
$^1$H NMRδ: 5.72–5.63(m,1H), 5.38–5.27(m,1H), 4.15–3.95(m,1H), 3.76(brs,1H), 2.62(t,J=8.0 Hz,2H), 1.31(d,J=6.6 Hz,3H), 1.25(s,6H), 0.93(s,3H), 0.70(s,3H).
MS m/z: 434(M$^+$), 69(100%).
UV $\lambda_{max}$ nm: 272, 282, 293.

EXAMPLE 16

1α,3β-Dihydroxy-20(S)-(4-ethyl-4-hydroxyhexylthio)pregna-5,7-diene

After the same reaction as in Example 15 was conducted using the 20S-isomer obtained in Example 8 (8.6 mg, 15.3 μmol), dry tetrahydrofuran (1.5 ml) and lithium aluminum hydride (1.7 mg, 46.0 μmol), the residue was purified by preparative thin-layer chromatography (1 plate, dichloromethane:ethanol=8:1, developed once) to give the title compound as a white solid (5.7 mg, 78%).

IR(neat): 3400, 2950, 1460, 1370, 1050 cm$^{-1}$.
$^1$H NMRδ: 5.77–5.64(m,1H), 5.43–5.34(m,1H), 4.12–4.00(m,1H), 3.77(brs,1H), 1.47(q,J=7.3 Hz,4H), 1.40(d,J=6.3 Hz,3H), 0.95(s,3H), 0.86(t,J=7.3 Hz,6H), 0.66(s,3H).
MS m/z: 476(M$^+$), 143(100%).
UV $\lambda_{max}$ nm: 271, 282, 294.

EXAMPLE 17

1α,3β-Dihydroxy-20(R)-(4-ethyl-4-hydroxyhexylthio)pregna-5,7-diene

After the same reaction as in Example 15 was conducted using the 20R-isomer obtained in Example 8 (21.1 mg, 37.6

μmol), dry tetrahydrofuran (2 ml) and lithium aluminum hydride (4.3 mg, 0.113 mmol), the residue was purified by preparative thin-layer chromatography (1 plate, dichloromethane:ethanol=8:1, developed once) to give the title compound as a white solid (16.0 mg, 89%).

IR(KBr): 3400, 2950, 1460, 1370, 1050 cm$^{-1}$.
$^1$H NMRδ: 5.76–5.68(m,1H), 5.43–5.34(m,1H), 4.15–4.00(m,1H), 3.78(brs,1H), 1.47(q,J=7.3 Hz,4H), 1.29 (d,J=6.3 Hz,3H), 0.95(s,3H), 0.86(t,J=7.3 Hz,6H), 0.71(s, 3H).
MS m/z: 476(M$^+$), 143(100%).
UV $\lambda_{max}$ nm: 271, 282, 294.

EXAMPLE 18

1α,3β-Dihydroxy-20(S)-(4-hydroxy-4-methylpentylthio)pregna-5,7-diene

Under an argon atmosphere, to a solution of the 20S-isomer obtained in Example 14 (12.9 mg, 22.9 μmol) in dry tetrahydrofuran (1.5 ml) was added tetra-n-butylammonium fluoride (1M solution in tetrahydrofuran, 1 ml), and the mixture was gently refluxed for 16 hours. The reaction mixture was poured into water and extracted with ethyl acetate. The organic layer was washed with an aqueous saturated sodium bicarbonate solution and brine, dried over magnesium sulfate, and the solvent was removed under reduced pressure. The residue was purified by preparative thin-layer chromatography (1 plate, dichloromethane:ethanol=9:1, developed once) to give the title compound as a colorless oil (7.7 mg, 75%).

IR(neat): 3400, 2950, 1460, 1370, 1050 cm$^{-1}$.
$^1$H NMRδ: 5.72–5.64(m,1H), 5.39–5.29(m,1H), 4.23–3.42(m,1H), 3.77(brs,1H), 1.40(d,J=6.6 Hz,3H), 1.23 (s,6H), 0.95(s,3H), 0.66(s,3H).
MS m/z: 448(M$^+$), 55(100%).
UV $\lambda_{max}$ nm: 271, 282, 294.

EXAMPLE 19

1α,3β-Dihydroxy-20(R)-(4-hydroxy-4-methylpentylthio)pregna-5,7-diene

The same reaction as in Example 18 was conducted using the 20R-isomer obtained in Example 14 (23.7 mg, 42.1 μmol), dry tetrahydrofuran (1.5 ml) and tetra-n-butylammonium fluoride (1M solution in tetrahydrofuran, 1 ml) to give the title compound as a colorless oil (10.0 mg, 53%).

IR(neat): 3400, 2950, 1460, 1370, 1060 cm$^{-1}$.
$^1$H NMRδ: 5.80–5.67(m,1H), 5.41–5.31(m,1H), 4.18–3.96(m,1H), 3.78(brs,1H), 1.29(d,J=6.6 Hz,3H), 1.22 (s,6H), 0.95(s,3H), 0.71(s,3H).
MS m/z: 448(M$^+$), 55(100%).
UV $\lambda_{max}$ nm: 271, 282, 294.

EXAMPLE 20

1α,3β-Dihydroxy-20(S)-(3-ethyl-3-hydroxypentylthio)pregna-5,7-diene

After the same synthetic reaction as in Example 15 was conducted using the 20S-isomer obtained in Example 10 (12.5 mg, 22.9 μmol), dry tetrahydrofuran (1 ml) and lithium aluminum hydride (2.6 mg, 68.7 μmol), the residue was purified by preparative thin-layer chromatography (1 plate, dichloromethane:ethanol=9:1, developed once) to give the title compound as a colorless oil (8.2 mg, 77%).

IR(neat): 3400, 2950, 1460, 1370, 1030 cm$^{-1}$.
$^1$H NMRδ: 5.76–5.67(m,1H), 5.40–5.30(m,1H), 4.15–3.99(m,1H), 3.76(brs,1H), 2.58(t,J=8.0 Hz,2H), 1.50 (q,J=7.3 Hz,4H), 1.41(d,J=6.8 Hz,3H), 0.95(s,3H), 0.87(t, J=7.3 Hz,6H), 0.67(s,3H).
MS m/z: 462(M$^+$), 55(100%).
UV $\lambda_{max}$ nm: 271, 282, 294.

EXAMPLE 21

1α,3β-Dihydroxy-20(R)-(3-ethyl-3-hydroxypentylthio)pregna-5,7-diene

After the same reaction as in Example 15 was conducted using the 20R-isomer obtained in Example 10 (28.2 mg, 51.6 μmol), dry tetrahydrofuran (2 ml) and lithium aluminum hydride (5.9 mg, 0.155 mmol), the residue was purified by preparative thin-layer chromatography (1 plate, dichloromethane:ethanol=9:1, developed once) to give the title compound as a colorless oil (8.2 mg, 77%).

IR(neat): 3400, 2950, 1460, 1370, 1030 cm$^{-1}$.
$^1$H NMRδ: 5.73–5.65(m,1H), 5.38–5.29(m,1H), 4.15–3.95(m,1H), 3.77(brs,1H), 2.56(t,J=8.0 Hz,2H), 1.49 (q,J=7.3 Hz,4H), 1.31(d,J=6.6 Hz,3H), 0.94(s,3H), 0.87(t, J=7.3 Hz,6H), 0.71(s,3H).
MS m/z: 462(M$^+$), 55(100%).
UV $\lambda_{max}$ nm: 271, 282, 294.

EXAMPLE 22

1α,3β-Dihydroxy-20(S)-(5-hydroxy-5-methylhexylthio)pregna-5,7-diene

After the same reaction as in Example 15 was conducted using the 20S-isomer obtained in Example 11 (10.6 mg, 19.4 μmol), dry tetrahydrofuran (1 ml) and lithium aluminum hydride (2.5 mg, 65.8 μmol), the residue was purified by preparative thin-layer chromatography (1 plate, dichloromethane:ethanol=7:1, developed once) to give the title compound as a white solid (6.1 mg, 68%).

IR(neat): 3400, 2950, 1460, 1370, 1050 cm$^{-1}$.
$^1$H NMRδ: 5.79–5.68(m,1H), 5.43–5.35(m,1H), 4.13–3.97(m,1H), 3.75(brs,1H), 1.40(d,J=6.6 Hz,3H), 1.22 (s,6H), 0.94(s,3H), 0.66(s,3H).
MS m/z: 462(M$^+$), 131(100%).
UV $\lambda_{max}$ nm: 271, 282, 294.

EXAMPLE 23

1α,3β-Dihydroxy-20(R)-(5-hydroxy-5-methylhexylthio)pregna-5,7-diene

After the same reaction as in Example 15 was conducted using the 20R-isomer obtained in Example 11 (36.5 mg, 69.1 μmol), dry tetrahydrofuran (2 ml) and lithium aluminum hydride (7.9 mg, 0.207 mmol), the residue was purified by preparative thin-layer chromatography (1 plate, dichloromethane:ethanol=7:1, developed once) to give the title compound as a colorless oil (25.0 mg, 78%).

IR(neat): 3400, 2950, 1460, 1370, 1050 cm$^{-1}$.
$^1$H NMRδ: 5.73–5.65(m,1H), 5.39–5.30(m,1H), 4.14–3.95(m,1H), 3.77(brs,1H), 1.29(d,J=6.3 Hz,3H), 1.21 (s,6H), 0.94(s,3H), 0.70(s,3H).
MS m/z: 462(M$^+$), 131(100%).
UV $\lambda_{max}$ nm: 271, 282, 294.

EXAMPLE 24

1α,3β-Dihydroxy-20(S)-(6-hydroxy-6-methylheptylthio)pregna-5,7-diene

After the same reaction as in Example 15 was conducted using the mixture of the 20S-isomer and the starting thiol obtained in Example 12 (33.9 mg), dry tetrahydrofuran (1 ml) and lithium aluminum hydride (20.0 mg, 0.527 mmol), the residue was purified by preparative thin-layer chromatography (1 plate, dichloromethane:ethanol=7:1, developed once) to give the title compound as a colorless oil (5.8 mg).

IR(neat): 3400, 2940, 1460, 1370, 1050 cm$^{-1}$.

$^1$H NMRδ: 5.75–5.68(m,1H), 5.42–5.33(m,1H), 4.12–3.97(m,1H), 3.75(brs,1H), 1.40(d,J=6.6 Hz,3H), 1.21(s,6H), 0.94(s,3H), 0.66(s,3H).

MS m/z: 476(M$^+$), 171(100%).

UV $\lambda_{max}$ nm: 271, 282, 294.

EXAMPLE 25

1α,3β-Dihydroxy-20(R)-(6-hydroxy-6-methylheptylthio)pregna-5,7-diene

After the same reaction as in Example 15 was conducted using the 20R-isomer obtained in Example 12 (26.4 mg, 47.1 μmol), dry tetrahydrofuran (2 ml) and lithium aluminum hydride (5.4 mg, 0.141 mmol), the residue was purified by preparative thin-layer chromatography (1 plate, dichloromethane:ethanol=7:1, developed once) to give the title compound as a colorless oil (15.0 mg, 67%).

IR(neat): 3400, 2940, 1460, 1370, 1050 cm$^{-1}$.

$^1$H NMRδ: 5.75–5.65(m,1H), 5.39–5.30(m,1H), 4.14–3.96(m,1H), 3.78(brs,1H), 1.29(d,J=6.3 Hz,3H), 1.21(s,6H), 0.95(s,3H), 0.71(s,3H).

MS m/z: 476(M$^+$), 171(100%).

UV $\lambda_{max}$ nm: 271, 282, 294.

EXAMPLE 26

1α,3β-Dihydroxy-20(S)-(3-hydroxy-3-n-propylhexylthio)pregna-5,7-diene

After the same reaction as in Example 15 was conducted using the 20S-isomer obtained in Example 13 (35.9 mg, 62.4 μmol), dry tetrahydrofuran (3 ml) and lithium aluminum hydride (7.1 mg, 0.187 mmol), the residue was purified by preparative thin-layer chromatography (1 plate, dichloromethane:ethanol=6:1, developed once) to give the title compound as a colorless oil (21.4 mg, 70%).

IR(neat): 3400, 2950, 1460, 1370, 1030 cm$^{-1}$.

$^1$H NMRδ: 5.76–5.66(m,1H), 5.42–5.32(m,1H), 4.16–3.96(m,1H), 3.76(brs,1H), 2.58(t,J=8.0 Hz,2H), 0.94(s,3H), 0.92(t,J=6.8 Hz,6H), 0.66(s,3H).

MS m/z: 490(M$^+$), 157(100%).

UV $\lambda_{max}$ nm: 271, 282, 294.

EXAMPLE 27

1α,3β-Dihydroxy-20(R)-(3-hydroxy-3-n-propylhexylthio)pregna-5,7-diene

After the same reaction as in Example 15 was conducted using the 20R-isomer obtained in Example 13 (126 mg, 0.220 mmol), dry tetrahydrofuran (10 ml) and lithium aluminum hydride (25 mg, 0.660 mmol), the residue was purified by preparative thin-layer chromatography (2 plates, dichloromethane:ethanol=6:1, developed once) to give the title compound as a white solid (74.4 mg, 69%).

IR(neat): 3400, 2950, 1460, 1370, 1050 cm$^{-1}$.

$^1$H NMRδ: 5.75–5.63(m,1H), 5.41–5.29(m,1H), 4.16–3.93(m,1H), 3.75(brs,1H), 2.55(t,J=7.8 Hz,2H), 1.00–0.84(s and t,9H), 0.70(s,3H).

MS m/z: 490(M$^+$), 157(100%).

UV $\lambda_{max}$ nm: 271, 282, 294.

EXAMPLE 28

1α,3β-Dihydroxy-20(S)-(3-hydroxy-3-methylbutylthio)-9,10-secopregna-5,7,10(19)-triene The 20S-isomer obtained in Example 15 (10.1 mg, 23.2 μmol) was dissolved into ethanol (200 ml) and irradiated using a 400 W high-pressure mercury lamp with a Vycor filter for 2 minutes under bubbling with argon at 0° C., and then gently refluxed for 2 hours. The solvent was removed and the residue was purified by preparative thin-layer chromatography (1 plate, dichloromethane:ethanol=10:1, developed 3 times) to give the title compound as a colorless oil (1.7 mg, 17%).

IR(neat): 3380, 2920, 1440, 1370, 1050 cm$^{-1}$.

$^1$H NMRδ: 6.37(d,J=11.1 Hz,1H), 6.02(d,J=11.1 Hz,1H), 5.33(s,1H), 5.00(s,1H), 4.48–4.35(br,1H), 4.30–4.17(br, 1H), 2.63(t,J=7.8 Hz,2H), 1.39(d,J=6.6 Hz,3H), 1.25(s,6H), 0.58(s,3H).

MS m/z: 434(M$^+$), 69(100%).

UV $\lambda_{max}$ nm: 263, $\lambda_{min}$ nm: 227.

EXAMPLE 29

1α,3β-Dihydroxy-20(R)-(3-hydroxy-3-methylbutylthio)-9,10-secopregna-5,7,10(19)-triene After the same reaction as in Example 28 (irradiation for 3.75 minutes) was conducted using the 20R-isomer obtained in Example 15 (19.3 mg, 44.4 μmol), the residue was purified by preparative thin-layer chromatography (1 plate, dichloromethane:ethanol=10:1, developed 3 times) to give the title compound as a colorless oil (1.6 mg, 8%).

IR(neat): 3390, 2920, 1450, 1380, 1060 cm$^{-1}$.

$^1$H NMRδ: 6.37(d,J=11.1 Hz,1H), 6.01(d,J=11.1 Hz,1H), 5.33(s,1H), 5.00(s,1H), 4.48–4.36(br,1H), 4.30–4.13(br, 1H), 2.61(t,J=8.3 Hz,2H), 1.30(d,J=6.6 Hz,3H), 1.25(s,6H), 0.62(s,3H).

MS m/z: 434(M$^+$), 69(100%).

UV $\lambda_{max}$ nm: 263, $\lambda_{min}$ nm: 227.

EXAMPLE 30

1α,3β-Dihydroxy-20(S)-(4-ethyl-4-hydroxyhexylthio)-9,10-secopregna-5,7,10(19)-triene After the same reaction as in Example 28 (irradiation for 1.5 minutes) was conducted using the compound obtained in Example 16 (5.1 mg, 10.7 μmol), the residue was purified by preparative thin-layer chromatography (1 plate, dichloromethane:ethanol=9:1, developed twice) to give the title compound as a colorless oil (1.1 mg, 22%).

IR(neat): 3400, 2950, 1450, 1370, 1050 cm$^{-1}$.

$^1$H NMRδ: 6.37(d,J=11.1 Hz,1H), 6.02(d,J=11.1 Hz,1H), 5.33(s,1H), 5.00(s,1H), 4.50–4.38(br,1H), 4.30–4.17(br, 1H), 1.47(q,J=7.3 Hz,4H), 1.38(d,J=6.3 Hz,3H), 0.86(t,J= 7.3 Hz,6H), 0.58(s,3H).

MS m/z: 476(M$^+$), 69(100%).

UV $\lambda_{max}$ nm: 263, $\lambda_{min}$ nm: 227.

EXAMPLE 31

1α,3β-Dihydroxy-20(R)-(4-ethyl-4-hydroxyhexylthio)-9,10-secopregna-5,7,10(19)-triene After the same reaction as in Example 28 (irradiation for 2.5 minutes) was conducted using the compound obtained in Example 17 (16.0 mg, 33.6 μmol), the residue was purified by preparative thin-layer chromatography (1 plate, dichloromethane:ethanol=9:1, developed 3 times, then 1 plate, hexane:ethyl acetate:ethanol=5:5:0.3, developed 3 times) to give the title compound as a colorless oil (2.2 mg, 14%).

IR(neat): 3400, 2950, 1460, 1380, 1060 cm$^{-1}$.

$^1$H NMRδ: 6.38(d,J=11.2 Hz,1H), 6.01(d,J=11.2 Hz,1H), 5.33(s,1H), 5.00(s,1H), 4.52–4.38(br,1H), 4.29–4.16(br,1H), 1.47(q,J=7.3 Hz,4H), 1.28(d,J=6.6 Hz,3H), 0.68(t,J=7.3 Hz,6H), 0.62(s,3H).

MS m/z: 476(M$^+$), 69(100%).

UV $\lambda_{max}$ nm: 263, $\lambda_{min}$ nm: 227.

EXAMPLE 32

1α,3β-Dihydroxy-20(S)-(4-hydroxy-4-methylpentylthio)-9,10-secopregna-5,7,10(19)-triene After the same reaction as in Example 28 (irradiation for 1.75 minutes) was conducted using the compound obtained in Example 18 (7.7 mg, 17.2 μmol), the residue was purified by preparative thin-layer chromatog-raphy (1 plate, dichloromethane:ethanol=9:1, developed 3 times) to give the title compound as a colorless oil (2.0 mg, 26%).

IR(neat): 3400, 2950, 1450, 1380 cm$^{-1}$.

$^1$H NMRδ: 6.37(d,J=11.2 Hz,1H), 6.02(d,J=11.2 Hz,1H), 5.33(s,1H), 5.00(s,1H), 4.48–4.35(br,1H), 4.28–4.16(br,1H), 1.38(d,J=6.3 Hz,3H), 1.22(s,6H), 0.58(s,3H).

MS m/z: 448(M$^+$), 117(100%).

UV $\lambda_{max}$ nm: 262, $\lambda_{min}$ nm: 227.

EXAMPLE 33

1α,3β-Dihydroxy-20(R)-(4-hydroxy-4-methylpentylthio)-9,10-secopregna-5,7,10(19)-triene After the same reaction as in Example 28 (irradiation for 1.25 minutes) was conducted using the compound obtained in Example 19 (10.0 mg, 22.3 μmol), the residue was purified by preparative thin-layer chromatog-raphy (1 plate, dichloromethane:ethanol=9:1, developed 3 times) to give the title compound as a colorless oil (1.9 mg, 19%).

IR(neat): 3400, 2950, 1450, 1380, 1060 cm$^{-1}$.

$^1$H NMRδ: 6.38(d,J=11.2 Hz,1H), 6.01(d,J=11.2 Hz,1H), 5.33(s,1H), 5.00(s,1H), 4.48–4.37(br,1H), 4.28–4.16(br,1H), 1.28(d,J=6.6 Hz,3H), 1.22(s,6H), 0.62(s,3H).

MS m/z: 448(M$^+$), 117(100%).

UV $\lambda_{max}$ nm: 262, $\lambda_{min}$ nm: 227.

EXAMPLE 34

1α,3β-Dihydroxy-20(S)-(3-ethyl-3-hydroxypentylthio)-9,10-secopregna-5,7,10(19)-triene After the same reaction as in Example 28 (irradiation for 1.5 minutes) was conducted using the compound obtained in Example 20 (8.2 mg, 17.7 μmol), the residue was purified by preparative thin-layer chromatography (1 plate, dichloromethane:ethanol=9:1, developed 3 times) to give the title compound as a colorless oil (1.7 mg, 21%).

IR(neat): 3400, 2950, 1460, 1370, 1050 cm$^{-1}$.

$^1$H NMRδ: 6.37(d,J=11.2 Hz,1H), 6.02(d,J=11.2 Hz,1H), 5.33(s,1H), 5.00(s,1H), 4.49–4.40(br,1H), 4.29–4.18(br,1H), 2.58(t,J=7.9 Hz,2H), 1.49(q,J=7.3 Hz,4H), 1.39(d,J=6.6 Hz,3H), 0.87(t,J=7.3 Hz,6H), 0.58(s,3H).

MS m/z: 462(M$^+$), 55(100%).

UV $\lambda_{max}$ nm: 262, $\lambda_{min}$ nm: 227.

EXAMPLE 35

1α,3β-Dihydroxy-20(R)-(3-ethyl-3-hydroxypentylthio)-9,10-secopregna-5,7,10(19)-triene After the same reaction as in Example 28 (irradiation for 3.25 minutes) was conducted using the compound obtained in Example 21 (20.9 mg, 45.2 μmol), the residue was purified by preparative thin-layer chromatography (1 plate, dichloromethane:ethanol=9:1, developed 3 times then 1 plate hexane:ethyl acetate:ethanol=5:5:0.3, developed 4 times) to give the title compound as a colorless oil (2.3 mg, 11%).

IR(neat): 3400, 2950, 1460, 1370, 1050 cm$^{-1}$.

$^1$H NMRδ: 6.38(d,J=11.2 Hz,1H), 6.01(d,J=11.2 Hz,1H), 5.33(s,1H), 5.00(s,1H), 4.48–4.40(br,1H), 4.30–4.15(br,1H), 2.55(t,J=7.9 Hz,2H), 1.52(q,J=7.3 Hz,4H), 1.30(d,J=6.6 Hz,3H), 0.87(t,J=7.3 Hz,6H), 0.62(s,3H).

MS m/z: 462(M$^+$), 55(100%).

UV $\lambda_{max}$ nm: 263, $\lambda_{min}$ nm: 227.

EXAMPLE 36

1α,3β-Dihydroxy-20(S)-(5-hydroxy-5-methylhexylthio)-9,10-secopregna-5,7,10(19)-triene After the same reaction as in Example 28 (irradiation for 1.75 minutes) was conducted using the compound obtained in Example 22 (6.1 mg, 13.2 μmol), the residue was purified by preparative thin-layer chromatography (1 plate, dichloromethane:ethanol=12:1, developed 3 times) to give the title compound as a colorless oil (1.2 mg, 20%).

IR(neat): 3400, 2950, 1460, 1370, 1050 cm$^{-1}$.

$^1$H NMRδ: 6.37(d,J=11.2 Hz,1H), 6.02(d,J=11.2 Hz,1H), 5.33(s,1H), 5.00(s,1H), 4.48–4.37(br,1H), 4.29–4.13(br,1H), 1.38(d,J=6.3 Hz,3H), 1.22(s,6H), 0.58(s,3H).

MS m/z: 462(M$^+$), 131(100%).

UV $\lambda_{max}$ nm: 262, $\lambda_{min}$ nm: 227.

EXAMPLE 37

1α,3β-Dihydroxy-20(R)-(5-hydroxy-5-methylhexylthio)-9,10-secopregna-5,7,10(19)-triene After the same reaction as in Example 28 (irradiation for 3.5 minutes) was conducted using the compound obtained in Example 23 (25.0 mg, 54.0 μmol), the residue was purified by preparative thin-layer chromatography (1 plate, dichloromethane:ethanol=12:1, developed 4 times then 1 plate, hexane:ethyl acetate:ethanol=5:5:0.1, developed 3 times) to give the title compound as a colorless oil (2.3 mg, 9%).

IR(neat): 3400, 2950, 1460, 1380, 1060 cm$^{-1}$.

$^1$H NMRδ: 6.38(d,J=11.2 Hz,1H), 6.01(d,J=11.2 Hz,1H), 5.33(s,1H), 5.00(s,1H), 4.50–4.35(br,1H), 4.28–4.16(br,1H), 1.28(d,J=6.8 Hz,3H), 1.21(s,6H), 0.62(s,3H).

MS m/z: 462(M$^+$), 131(100%).

UV $\lambda_{max}$ nm: 263, $\lambda_{min}$ nm: 227.

EXAMPLE 38

1α,3β-Dihydroxy-20(S)-(6-hydroxy-6-methylheptylthio)-9,10-secopregna-5,7,10(19)-triene After the same reaction as in Example 28 (irradiation for 1.75 minutes) was conducted using the compound obtained in Example 24 (5.8 mg, 12.2 μmol), the residue was purified by preparative thin-layer chromatography (1 plate, dichloromethane:ethanol=12:1, developed 4 times) to give the title compound as a colorless oil (0.99 mg, 17%).

IR(neat): 3400, 2950, 1460, 1370, 1050 cm$^{-1}$.

$^1$H NMRδ: 6.37(d,J=11.2 Hz,1H), 6.02(d,J=11.2 Hz,1H), 5.33(s,1H), 5.00(s,1H), 4.48–4.38(br,1H), 4.30–4.15(br, 1H), 1.38(d,J=6.6 Hz,3H), 1.21(s,6H), 0.58(s,3H).

MS m/z: 476(M$^+$), 60(100%).

UV $\lambda_{max}$ nm: 262, $\lambda_{min}$ nm: 227.

EXAMPLE 39

1α,3β-Dihydroxy-20(R)-(6-hydroxy-6-methylheptylthio)-9,10-secopregna-5,7,10(19)-triene After the same reaction as in Example 28 (irradiation for 2.5 minutes) was conducted using the compound obtained in Example 25 (15.0 mg, 31.5 μmol), the residue was purified by preparative thin-layer chromatography (1 plate, dichloromethane:ethanol=12:1, developed 3 times then 1 plate, hexane:ethyl acetate:ethanol=5:5:0.1, developed 4 times) to give the title compound as a colorless oil (2.0 mg, 13%).

IR(neat): 3400, 2950, 1460, 1370, 1050 cm$^{-1}$.

$^1$H NMRδ: 6.38(d,J=11.2 Hz,1H), 6.01(d,J=11.2 Hz,1H), 5.33(s,1H), 5.00(s,1H), 4.49–4.38(br,1H), 4.29–4.17(br, 1H), 1.28(d,J=6.6 Hz,3H), 1.21(s,6H), 0.62(s,3H).

MS m/z: 476(M$^+$), 60(100%).

UV $\lambda_{max}$ nm: 263, 80$_{min}$ nm: 227.

EXAMPLE 40

1α,3β-Dihydroxy-20(S)-(3-hydroxy-3-n-propylhexylthio)-9,10-secopregna-5,7,10(19)-triene After the same reaction as in Example 28 (irradiation for 3.5 minutes) was conducted using the compound obtained in Example 26 (20.2 mg, 41.2 μmol), the residue was purified by preparative thin-layer chromatography (1 plate, dichloromethane:ethanol=10:1, developed 3 times then 1 plate, hexane:ethyl acetate:ethanol=6:4:0.5, developed 3 times) to give the title compound as a colorless oil (1.8 mg, 9%).

IR(neat): 3400, 2950, 1450, 1370, 1050 cm$^{-1}$.

$^1$H NMRδ: 6.37(d,J=11.1 Hz,1H), 6.03(d,J=11.1 Hz,1H), 5.33(s,1H), 5.00(s,1H), 4.52–4.38(br,1H), 4.30–4.18(br, 1H), 2.57(t,J=8.0 Hz,2H), 0.93(t,J=6.8 Hz,6H), 0.58(s,3H).

MS m/z: 490(M$^+$), 157(100%).

UV $\lambda_{max}$ nm: 263, $\lambda_{min}$ nm: 227.

EXAMPLE 41

1α,3β-Dihydroxy-20(R)-(3-hydroxy-3-n-propylhexylthio)-9,10-secopregna-5,7,10(19)-triene After the same reaction as in Example 28, irradiation for 4.75 minutes) was conducted using the compound obtained in Example 27 (41.3 mg, 84.2 μmol), the residue was purified by preparative thin-layer chromatography (2 plates, dichloromethane:ethanol=10:1, developed 3 times then 1 plate, hexane:ethyl acetate:ethanol=6:4:0.5, developed 3 times) to give the title compound as a colorless oil (4.6 mg, 11%).

IR(neat): 3400, 2950, 1450, 1380, 1060 cm$^{-1}$.

$^1$H NMRδ: 6.38(d,J=11.2 Hz,1H), 6.01(d,J=11.2 Hz,1H), 5.33(s,1H), 5.00(s,1H), 4.48–4.38(br,1H), 4.30–4.16(br, 1H), 2.55(t,J=8.0 Hz,2H), 0.92(t,J=6.8 Hz,6H), 0.62(s,3H).

MS m/z: 490(M$^+$), 157(100%).

UV $\lambda_{max}$ nm: 263, $\lambda_{min}$ nm: 227.

EXAMPLE 42

1α,3β-Bis(t-butyldimethylsilyloxy)-16α-hydroxy-17-oxoandrosta-5,7-diene

Under an argon atmosphere, a solution of potassium t-butoxide (4.13 g, 36.8 mmol) in dry tetrahydrofuran (500 ml) was cooled to −78° C., and a solution of 1α,3β-bis(t-butyldimethylsilyloxy)-17-oxoandrosta-5,7-diene (13.0 g, 24.5 mmol) in tetrahydrofuran (40 ml) was added dropwise. After the mixture was stirred at the same temperature for 1 hour, a solution of 2-(phenylsulfonyl)-3-phenyloxazyldine (9.62 g, 36.8 mmol) in tetrahydrofuran (40 ml) was added dropwise and the mixture was further stirred at −78° C. for 1.5 hour. The reaction mixture was quenched with an aqueous saturated ammonium chloride solution, poured into water and extracted with ethyl acetate. The organic layer was washed with brine and dried over anhydrous magnesium sulfate. The mixture was concentrated under reduced pressure and the deposited solids were filtered, then the filtrate was concentrated again and the residue was purified by column chromatography on silica gel (hexane:ethyl acetate:chloroform=7:1:2) to give the title compound as a white solid (3.10 g, 23%).

IR(KBr): 3480, 2950, 2850, 1750, 1460, 1380, 1250, 1100 cm$^{-1}$.

$^1$H NMRδ: 0.05(s,6H), 0.07(s,3H), 0.11(s,3H), 0.88(s, 9H), 0.89(s,9H), 0.90(s,3H), 0.93(s,3H), 3.71(brs,1H), 3.97–4.16(m,1H), 4.42(d,J=8.0 Hz,1H), 5.43–5.51(m,1H), 5.56–5.64(m,1H).

MS(20 eV) m/z: 546(M$^+$), 355(100%).

UV $\lambda_{max}$ nm: 270, 281, 293.

EXAMPLE 43

1α,3β-Bis(t-butyldimethylsilyloxy)-16α-hydroxypregna-5,7,17(E)-triene and 1α,3β-bis(t-butyldimethylsilyloxy)-16α-hydroxypregna-5,7,17 (Z)-triene Under an argon atmosphere, the mixture of potassium t-butoxide (1.29 g, 11.4 mmol) and ethyltriphenyl phosphonium bromide (4.28 g, 11.4 mmol) in tetrahydrofuran (50 ml) was stirred at 60° C. for 1.5 hour and then returned to room temperature. A solution of the compound obtained in Example 42 (2.10 g, 3.84 mmol) in tetrahydrofuran (20 ml) was added and the mixture was further stirred at 60° C. for 1 hour. The reaction mixture was poured into water and extracted with ethyl acetate. The organic layer was washed with brine and dried over anhydrous magnesium sulfate, then the solvent was distilled off under reduced pressure. The residue was purified by column chromatography on silica gel (hexane:ethyl acetate=7:1) to give the title compounds E-isomer (375 mg, 18%) and Z-isomer (351 mg, 16%) as well as a mixture of the both isomers (142 mg, 6%).

E-isomer

IR(nujol): 3450, 2950, 2850, 1460, 1380, 1250, 1100, 1080 cm$^{-1}$.

$^1$H NMRδ: 0.06(s,3H), 0.07(s,6H), 0.11(s,3H), 0.59(s, 3H), 0.89(s,18H), 0.91(s,3H), 3.71(brs,1H), 3.84–4.12(m, 2H), 5.28–5.39(m,1H), 5.47–5.64(m,2H).

MS(20 eV) m/z: 558(M$^+$), 369(100%).

UV $\lambda_{max}$ nm: 270, 281, 293.

Z-isomer

IR(nujol): 3450, 2950, 2850, 1450, 1380, 1255, 1100 cm$^{-1}$.

$^1$H NMRδ: 0.05(s,3H), 0.06(s,6H), 0.11(s,3H), 0.70(s, 3H), 0.88(s,18H), 0.90(s,3H), 1.80(d,J=8.8 Hz,3H), 3.71 (brs,1H), 3.97–4.16(m,1H), 4.17–4.27(m,1H), 5.26–5.36(m, 1H), 5.52–5.70(m,2H).

MS(20 eV) m/z: 558(M$^+$), 369(100%).

UV λ$_{max}$ nm: 270, 282, 293.

EXAMPLE 44

1α,3β-Bis(t-butyldimethylsilyloxy)-16-oxopregna-5, 7,17(E)-triene

Under an argon atmosphere, a solution of trichloromethyl chloroformate (118 μl, 0.68 mmol) in dry dichloromethane (3 ml) was cooled to −78° C. and stirred with dimethyl sulfoxide (186 μl, 2.61 mmol) for 5 minutes, and a solution of the E-isomer from the compounds obtained in Example 43 (350 mg, 0.63 mmol) in dry dichloromethane (2 ml) was added dropwise. After the mixed solution was stirred at −78° C. for 15 minutes, triethylamine (435 μl, 3.10 mmol) was added, and the mixture was stirred at −78° C. for 15 minutes and at room temperature for 30 minutes. The reaction solution was poured into water and extracted with dichloromethane. The organic layer was washed with brine and dried over anhydrous magnesium sulfate, then the solvent was distilled off under reduced pressure. The residue was purified by column chromatography on silica gel (hexane:ethyl acetate=50:3) to give the title compound as a pale yellow solid (147 mg, 42%).

IR(KBr): 2950, 2850, 1730, 1650, 1460, 1380, 1250, 1100 cm$^{-1}$.

$^1$H NMRδ: 0.06(s,3H), 0.07(s,3H), 0.08(s,3H), 0.12(s, 3H), 0.87(s,3H), 0.89(s,18H), 0.99(s,3H), 1.88(d,J=7.4 Hz,3H), 3.73(brs,1H), 3.92–4.10(m,1H), 5.28–5.36(m,1H), 5.54–5.67(m,1H), 6.56(q,J=7.4 Hz,1H).

MS(20 eV) m/z: 556(M$^+$), 367(100%).

UV λ$_{max}$ nm: 242, 258, 270, 281, 293.

EXAMPLE 45

1α,3β-Bis(t-butyldimethylsilyloxy)-16-oxopregna-5, 7,17(Z)-triene

The same procedure as in Example 44 was followed using a solution of the Z-isomer from the compounds obtained in Example 43 (347 mg, 0.62 mmol) in dry dichloromethane (2 ml), a solution of trichloromethyl chloroformate (118 μl, 0.68 mmol) in dry dichloromethane (3 ml), dimethyl sulfoxide (186 μl, 2.61 mmol) and triethylamine (435 μl, 3.10 mmol) to give the title compound as a pale yellow solid (111 mg, 32%).

IR(KBr): 2950, 2850, 1720, 1640, 1460, 1380, 1255, 1080 cm$^{-1}$.

$^1$H NMRδ: 0.05(s,6H), 0.06(s,3H), 0.11(s,3H), 0.85(s, 3H), 0.86(s,9H), 0.88(s,9H), 0.93(s,3H), 2.16(d,J=7.4 Hz,3H), 3.72(brs,1H), 3.93–4.12(m,1H), 5.36–5.47(m,1H), 5.56–5.64(m,1H), 6.17(q,J=7.4 Hz,1H).

MS(20 eV) m/z: 556(M$^+$), 367(100%).

UV λ$_{max}$ nm: 242, 258, 270, 281, 293.

EXAMPLE 46

1α,3β-Bis(t-butyldimethylsilyloxy)-16-oxopregna-5, 7,17(E)-triene

The mixture of the E-isomer and Z-isomer from the compounds obtained in Example 43 (a mixture of about 1:1, 1.76 g, 3.15 mmol) was dissolved into chloroform (150 ml) and stirred with manganese dioxide (70 g) at room temperature for 1.5 hour. The reaction solution was filtered through Celite and the filtrate was concentrated, then the residue was purified by column chromatography on silica gel (hexane:ethyl acetate:chloroform=84:6:1) to give the title compound as a white solid (879 mg, 50%) and the starting Z-isomer (recovery 560 mg, 32%).

EXAMPLE 47

1α,3β-Bis(t-butyldimethylsilyloxy)-16-oxopregna-5, 7,17(Z)-triene

After the same reaction as in Example 44 was conducted using a solution of the Z-isomer recovered in Example 46 (533 mg, 0.95 mmol) in dry dichloromethane (1.5 ml), a solution of bis(trichloromethyl)carbonate (312 mg, 1.05 mmol) in dry dichloromethane (3 ml), dimethyl sulfoxide (284 μl, 4.00 mmol) and triethylamine (666 μl, 4.78 mmol), the residue was purified by column chromatography on silica gel (hexane:ethyl acetate=14:1) to give the title compound as a pale yellow solid (333 mg, 63%).

EXAMPLE 48

4-Phenyl-1,2,4-triazoline-3,5-dione adduct of 1α, 3β-bis(t-butyldimethylsilyloxy)pregna-5,7,17(E)-triene A solution of 1α,3β-bis(t-butyldimethylsilyloxy)pregna-5,7,17(E)-triene (1.00 g, 1.84 mmol) in dichloromethane (90 ml) was stirred with a solution of 4-phenyl-1,2,4-triazoline-3,5-dione (330 mg, 1.88 mmol) in dichloromethane (10 ml) at room temperature for 30 minutes, then the solvent was distilled off, and the residue was purified by column chromatography on silica gel (dichloromethane:ethyl acetate= 150:1) to give the title compound as a pale yellow solid (1.02 g, 77%).

$^1$H NMRδ: 0.07(s,3H), 0.08(s,3H), 0.10(s,3H), 0.13(s, 3H), 0.88(s,9H), 0.89(s,9H), 0.93(s,3H), 1.01(s,3H), 1.68(d, J=7.1 Hz,3H), 3.25(dd,J=4.0,14.0 Hz,1H), 3.85(t,J=2.7 Hz,1H), 4.79(m,1H), 5.17(q,J=7.1 Hz,1H), 6.22(d,J=8.2 Hz,1H), 6.38(d,J=8.2 Hz,1H), 7.19–7.49(m,5H).

UV λ$_{max}$ nm: 206, 258.

EXAMPLE 49

4-Phenyl-1,2,4-triazoline-3,5-dione adduct of 1α, 3β-bis(t-butyldimethylsilyloxy)-16α-hydroxypregna-5,7,17(E)-triene The compound obtained in Example 48 (931 mg, 1.3 mmol) was dissolved into dichloromethane (40 ml) and stirred with selenium dioxide (5.1 mg, 45.5 μmol) and t-butyl hydroperoxide (70%, 422 mg, 4.68 mmol) at room temperature for 27 hours. The reaction solution was diluted with dichloromethane, washed with brine, and dried over anhydrous magnesium sulfate, then the solvent was distilled off. The residue was purified by column chromatography on silica gel (dichloromethane:ethyl acetate=20:1) to give the title compound as a pale yellow solid (885 mg, 92%).

IR(neat): 2950, 2850, 1700, 1460, 1400, 1310, 1260, 1100, 1060 cm$^{-1}$.

$^1$H NMRδ: 0.07(s,3H), 0.09(s,3H), 0.10(s,3H), 0.13(s, 3H), 0.88(s,9H), 0.89(s,9H), 0.93(s,3H), 1.01(s,3H), 1.77(d, J=7.2 Hz,3H), 2.94(dd,J=4.6,11.7 Hz,1H), 3.25(dd,J=4.6, 12.3 Hz,1H), 3.85(brs,1H), 4.54(brs,1H), 4.78(m,1H), 5.69

(q,J=7.2 Hz,1H), 6.24(d,J=8.1 Hz,1H), 6.30(d,J=8.1 Hz,1H), 7.22–7.48(m,5H).

MS m/z: 733(M+), 73(100%).

UV $\lambda_{max}$ nm: 210, 258.

EXAMPLE 50

1α,3β-Bis(t-butyldimethylsilyloxy)-16α-hydroxypregna-5,7,17(E)-triene

The compound obtained in Example 49 (80.0 mg, 109 μmol) was dissolved into 1,3-dimethyl-2-imidazolidinone (6 ml) and the mixture was stirred at 140° C. for 16 hours. The mixture was poured into water and extracted with ethyl acetate. The organic layer was washed with brine and dried over anhydrous magnesium sulfate. The solvent was distilled off and the residue was purified by preparative thin-layer chromatography (1 plate, hexane:ethyl acetate=4:1, developed once) to give the title compound (39.2 mg, 64%).

EXAMPLE 51

1α,3β-Bis(t-butyldimethylsilyloxy)-20(S)-(3-hydroxy-3-methylbutylthio)-16-oxopregna-5,7-diene and 1α,3β-bis(t-butyldimethylsilyloxy)-20(R)-(3-hydroxy-3-methylbutylthio)-16-oxopregna-5,7-diene The compound obtained in Example 44 (140 mg, 251 μmol) was dissolved into tetrahydrofuran (4 ml) and stirred with 0.1M sodium tetraborate (4 ml) and 3-hydroxy-3-methylbutanethiol (121 μl) at room temperature for 12 hours. Then, water was added and the mixture was extracted with chloroform. The organic layer was washed with brine and dried over anhydrous magnesium sulfate. After the solvent was distilled off under reduced pressure, the residue was purified by preparative thin-layer chromatography (3 plates, hexane:ethyl acetate=3:1, developed 3 times) to give the title compounds S-isomer (115 mg, 68%) as a white solid and R-isomer (52.0 mg, 31%) as a colorless oil.

20S-isomer

IR(neat): 3460, 2950, 2850, 1740, 1460, 1380, 1260, 1100 cm$^{-1}$.

$^1$H NMRδ: 0.05(s,3H), 0.06(s,3H), 0.07(s,3H), 0.11(s,3H), 0.87(s,3H), 0.88(s,9H), 0.89(s,9H), 0.93(s,3H), 1.24(s,6H), 1.57(d,J=6.6 Hz,3H), 2.64(t,J=7.8 Hz,2H), 2.97–3.12 (m,1H), 3.73(brs,1H), 3.96–4.12(m,1H), 5.24–5.32(m,1H), 5.56–6.03(m,1H).

MS(20 eV) m/z: 676(M+), 365(100%).

UV $\lambda_{max}$ nm: 270, 281, 293.

20R-isomer

IR(neat): 3460, 2950, 2850, 1740, 1460, 1370, 1260, 1100 cm$^{-1}$.

$^1$H NMRδ: 0.05(s,6H), 0.07(s,3H), 0.11(s,3H), 0.86(s,3H), 0.87(s,9H), 0.89(s,9H), 0.94(s,3H), 1.23(s,6H), 1.44(d, J=6.3 Hz,3H), 2.60(t,J=8.2 Hz,2H), 3.25–3.38(m,1H), 3.70 (brs,1H), 3.95–4.10(m,1H), 5.44–5.52(m,1H), 5.58–5.65(m, 1H).

MS(20 eV) m/z: 676(M+), 365(100%).

UV $\lambda_{max}$ nm: 270, 281, 293.

EXAMPLE 52

1α,3β-Bis(t-butyldimethylsilyloxy)-20(S)-(3-hydroxy-3-methylbutylthio)-16-oxopregna-5,7-diene and 1α,3β-bis(t-butyldimethylsilyloxy)-20(R)-(3-hydroxy-3-methylbutylthio)-16-oxopregna-5,7-diene After the same reaction as in Example 51 was conducted using the compound obtained in Example 45 (80.0 mg, 144 μmol), 0.1M sodium tetraborate (2.3 ml), 3-hydroxy-3-methylbutanethiol (80 μl) and tetrahyrdrofuran (2.3 ml), the residue was purified by preparative thin-layer chromatography (2 plates, hexane:ethyl acetate=3:1, developed 3 times) to give the title compounds S-isomer (13.6 mg, 14%) and R-isomer (62.5 mg, 64%).

EXAMPLE 53

1α,3β-Bis(t-butyldimethylsilyloxy)-20(S)-(4-ethyl-4-hydroxyhexylthio)-16-oxopregna-5,7-diene and 1α,3β-bis(t-butyldimethylsilyloxy)-20(R)-(4-ethyl-4-hydroxyhexylthio)-16-oxopregna-5,7-diene After the same reaction as in Example 51 was conducted using the compound obtained in Example 44 (110 mg, 197 μmol), 0.1M sodium tetraborate (3 ml), 4-ethyl-4-hydroxyhexanethiol (100 μl) and tetrahydrofuran (3 ml), the residue was purified by preparative thin-layer chromatography (2 plates, dichloromethane:ethyl acetate:ethanol= 15:1:0.1, developed twice then 2 plates;, hexane:ethyl acetate=4:1, developed 5 times) to give the title compounds S-isomer (64.2 mg, 45%) and R-isomer (8.1 mg, 6%). After the same reaction as in Example 51 was conducted using the compound obtained in Example 45 (90.0 mg, 162 μmol), 0.1M sodium tetraborate (2.5 ml), 4-ethyl-4-hydroxyhexanethiol (90 μl) and tetrahydrofuran (2.5 ml), the residue was purified by preparative thin-layer chromatography (2 plates, dichloromethane:ethyl acetate:ethanol= 15:1:0.1, developed twice) to give the title compounds S-isomer (trace) and R-isomer (49.9 mg, 45%).

20S-isomer:

IR(neat): 3500, 2950, 2850, 1740, 1460, 1370, 1250, 1100, 1010 cm$^{-1}$.

$^1$H NMRδ: 0.06(s,3H), 0.07(s,3H), 0.08(s,3H), 0.12(s, 3H), 0.80–0.98(m,30H), 1.46(q,J=7.3 Hz,4H), 1.56(d,J=6.6 Hz,3H), 2.90–3.08(m,1H), 3.73(brs,1H), 3.93–4.15(m,1H), 5.23–5.32(m,1H), 5.54–5.64(m,1H).

MS m/z: 718(M+), 73(100%).

UV $\lambda_{max}$ nm: 270, 281, 293.

20R-isomer:

IR(neat): 3500, 2950, 2860, 1740, 1460, 1380, 1260, 1100, 1010 cm$^{-1}$.

$^1$H NMRδ: 0.06(s,6H), 0.07(s,3H), 0.11(s,3H), 0.76–0.94 (m,30H), 3.23–3.38(m,1H), 3.71(brs,1H), 3.96–4.13(m,1H), 5.46–5.54(m,1H), 5.59–5.66(m,1H).

MS m/z: 718(M+), 73(100%).

UV $\lambda_{max}$ nm: 270, 281, 293.

EXAMPLE 54

1α,3β-Bis(t-butyldimethylsilyloxy)-20(S)-(4-hydroxy-4-methylpentylthio)-16-oxopregna-5,7-diene and 1α,3β-bis(t-butyldimethylsilyloxy)-20(R)-(4-hydroxy-4-methylpentylthio)-16-oxopregna-5,7-diene After the same reaction as in Example 51 was conducted using the compound obtained in Example 44 (100 mg, 180 μmol), 0.1M sodium tetraborate (3 ml), 4-hydroxy-4-methyl-1-pentanethiol (100 μl) and tetrahydrofuran (3 ml), the residue was purified by preparative thin-layer chromatography (2 plates, hexane:ethyl acetate=3:1, developed 3 times) to give the title compounds S-isomer (85.8 mg, 69%) and R-isomer (19.7 mg, 16%). After the same reaction as in Example 51 was conducted using the compound obtained in Example 45 (80.0 mg, 144 μmol), 0.1M sodium tetraborate (2.3 ml), 4-hydroxy-4-methyl-1-pentanethiol (100 μl) and tetrahydrofuran (2.3 ml), the residue was purified by preparative thin-layer chromatography (2 plates, hexane:ethyl acetate=3:1, developed 3 times) to give the title compounds S-isomer (trace) and R-isomer (91.7 mg, 92%).

20S-isomer:

IR(neat): 3450, 2950, 2850, 1740, 1460, 1380, 1260, 1100 cm$^{-1}$.

$^1$H NMRδ: 0.06(s,3H), 0.07(s,3H), 0.08(s,3H), 0.12(s, 3H), 0.87(s,3H), 0.89(s,9H), 0.90(s,9H), 0.94(s,3H), 1.22(s, 6H), 1.56(d,J=6.6 Hz,3H), 2.97–3.05(m,1H), 3.72(brs,1H), 3.95–4.16(m,1H), 5.23–5.34(m,1H), 5.56–5.64(m,1H).

MS m/z: 690(M$^+$), 73(100%).

UV λ$_{max}$ nm: 270, 281, 293.

20R-isomer:

IR(neat): 3450, 2950, 2850, 1740, 1460, 1380, 1250, 1100 cm$^{-1}$.

$^1$H NMRδ: 0.06(s,6H), 0.07(s,3H), 0.11(s,3H), 0.84(s, 3H), 0.88(s,9H), 0.89(s,9H), 0.94(s,3H), 1.23(s,6H), 1.42(d, J=6.4 Hz,3H), 3.21–3.39(m,1H), 3.71(brs,1H), 3.94–4.14 (m,1H), 5.45–5.56(m,1H), 5.59–5.67(m,1H).

MS m/z: 690(M$^+$), 73(100%).

UV λ$_{max}$ nm: 270, 281, 293.

EXAMPLE 55

1α,3β-Bis(t-butyldimethylsilyloxy)-20(S)-(3-ethyl-3-hydroxypentylthio)-16-oxopregna-5,7-diene and 1α,3β-bis(t-butyldimethylsilyloxy)-20(R)-(3-ethyl-3-hydroxypentylthio)-16-oxopregna-5,7-diene After the same reaction as in Example 51 was conducted using the compound obtained in Example 44 (152 mg, 273 μmol), 0.1M sodium tetraborate (4.2 ml), 3-ethyl-3-hydroxy-1-pentanethiol (140 μl) and tetrahydrofuran (4.2 ml), the residue was purified by preparative thin-layer chromatography (2 plates, hexane:ethyl acetate=3:1, developed 3 times then 2 plates, dichloromethane:ethyl acetate:ethanol=15:1:0.1, developed twice) to give the title compounds S-isomer (100 mg, 52%) and R-isomer (17.7 mg, 9%). After the same reaction as in Example 51 was conducted using the compound obtained in Example 45 (42.1 mg, 75.6 μmol), 0.1M sodium tetraborate (1.2 ml), 3-ethyl-3-hydroxy-1-pentanethiol (40 μl) and tetrahydrofuran (1.2 ml), the residue was purified by preparative thin-layer chromatography (1 plate, hexane:ethyl acetate=4:1, developed 3 times) to give the title compounds S-isomer (trace) and R-isomer (34.3 mg, 64%).

20S-isomer:

IR(neat): 3500, 2950, 2850, 1740, 1460, 1380, 1250, 1100, 1010 cm$^{-1}$.

$^1$H NMRδ: 0.06(s,3H), 0.07(s,3H), 0.08(s,3H), 0.12(s, 3H), 0.80–0.98(m,30H), 1.46(q,J=7.3 Hz,4H), 2.59(t,J=8.3 Hz,2H), 2.95–3.09(m,1H), 3.72(brs,1H), 3.94–4.16(m,1H), 5.23–5.34(m,1H), 5.56–5.64(m,1H).

MS m/z: 704(M$^+$), 73(100%).

UV λ$_{max}$ nm: 270, 281, 293.

20R-isomer:

IR(neat): 3500, 2950, 2850, 1740, 1460, 1370, 1250, 1100, 1010 cm$^{-1}$.

$^1$H NMRδ: 0.06(s,6H), 0.07(s,3H), 0.11(s,3H), 0.76–0.94 (m,30H), 3.23–3.38(m,1H), 3.71(brs,1H), 3.96–4.13(m,1H), 5.46–5.54(m,1H), 5.59–5.65(m,1H).

MS m/z: 704(M$^+$), 73(100%).

UV λ$_{max}$ nm: 270, 281, 293.

EXAMPLE 56

1α,3β-Bis(t-butyldimethylsilyloxy)-20(S)-(3-hydroxy-3-methylbutylthio)-16β-hydroxypregna-5,7-diene and 1α,3β-bis(t-butyldimethylsilyloxy)-20(S)-(3-hydroxy-3-methylbutylthio)-16α-hydroxypregna-5,7-diene The 20S-isomer from the compounds obtained in Example 51 (113 mg, 167 μmol) was dissolved into tetrahydrofuran (3.5 ml) and lithium aluminum hydride (10.1 mg, 266 μmol) was added by portions. The mixture was stirred at room temperature for 30 minutes, then quenched with a 10% aqueous sodium hydroxide solution. Water was added and the mixture was extracted with ethyl acetate. The organic layer was washed with brine and dried over anhydrous magnesium sulfate. The solvent was distilled off and the residue was purified by preparative thin-layer chromatography (2 plates, hexane:ethyl acetate=1:1, developed twice) to give the title compounds β-isomer (73.4 mg, 65%) as a white solid and α-isomer (22.0 mg, 19%) as a colorless oil.

16β-isomer:

IR(KBr): 3450, 2950, 2850, 1460, 1370, 1250, 1100 cm$^{-1}$.

$^1$H NMRδ: 0.05(s,6H), 0.06(s,3H), 0.10(s,3H), 0.87(s, 9H), 0.88(s,9H), 0.91(s,3H), 0.93(s,3H), 1.25(s,6H), 1.48(d, J=6.2 Hz,3H), 2.65(t,J=8.1 Hz,2H), 3.11–3.25(m,1H), 3.70 (brs,1H), 3.97–4.13(m,1H), 4.38–4.55(m,1H), 5.27–5.36(m, 1H), 5.47–5.63(m,1H).

MS m/z: 678(M$^+$), 73(100%).

UV λ$_{max}$ nm: 271, 282, 294.

16α-isomer:

IR(neat): 3400, 2950, 2850, 1460, 1380, 1250, 1100 cm$^{-1}$.

$^1$H NMRδ: 0.05(s,3H), 0.06(s,6H), 0.10(s,3H), 0.72(s, 3H), 0.88(s,21H), 1.25(s,6H), 1.48(d,J=6.5 Hz,3H), 2.65(t, J=8.0 Hz,2H), 2.84–3.02(m,1H), 3.70(brs,1H), 3.97–4.28 (m,2H), 5.25–5.34(m,1H), 5.55–5.63(m,1H).

MS m/z: 678(M$^+$), 73(100%).

UV λ$_{max}$ nm: 270, 281, 293.

EXAMPLE 57

1α,3β-Bis(t-butyldimethylsilyloxy)-20(R)-(3-hydroxy-3-methylbutylthio)-16β-hydroxypregna-5,7-diene and 1α,3β-bis(t-butyldimethylsilyloxy)-20(R)-(3-hydroxy-3-methylbutylthio)-16α-hydroxypregna-5,7-diene After the same reaction as in Example 56 was conducted using the 20R-isomer from the compounds obtained in Example 51 (51.7 mg, 76.3 μmol), tetrahydrofuran (1.5 ml) and lithium aluminum hydride (4.6 mg, 122 μmol), the residue was purified by preparative thin-layer chromatography (1 plate, hexane:ethyl acetate=1:1, developed twice) to give the title compounds β-isomer (13.2 mg, 25%) and α-isomer (10.1 mg, 19%) both as colorless oils.

16β-isomer:

IR(neat): 3450, 2950, 2850, 1460, 1380, 1250, 1100 cm$^{-1}$.

$^1$H NMRδ: 0.05(s,3H), 0.06(s,6H), 0.11(s,3H), 0.79(s, 3H), 0.88(s,18H), 0.92(s,3H), 1.25(s,6H), 1.44(d,J=6.6 Hz,3H), 2.69(t,J=8.1 Hz,2H), 3.06–3.19(m,1H), 3.71(brs, 1H), 3.81–3.95(m,1H), 3.96–4.11(m,1H), 5.31–5.39(m,1H), 5.55–5.63(m,1H).

MS m/z: 678(M⁺), 73(100%).

UV $\lambda_{max}$ nm: 270, 282, 293.

16α-isomer:

IR(neat): 3450, 2950, 2850, 1460, 1380, 1250, 1100 cm⁻¹.

¹H NMRδ: 0.05(brs,9H), 0.11(s,3H), 0.84(s,3H), 0.88(s, 18H), 0.91(s,3H), 1.26(s,6H), 1.46(d,J=6.6 Hz,3H), 2.70(t, J=8.1 Hz,2H), 3.02–3.19(m,1H), 3.69(brs,1H), 3.95–4.11 (m,1H), 4.39–4.53(m,1H), 5.33–5.42(m,1H), 5.56–5.66(m, 1H).

MS m/z: 678(M⁺), 73(100%).

UV $\lambda_{max}$ nm: 270, 282, 293.

EXAMPLE 58

1α,3β-Bis(t-butyldimethylsilyloxy)-20(S)-(4-ethyl-4-hydroxyhexylthio)-16β-hydroxypregna-5,7-diene and 1α,3β-bis(t-butyldimethylsilyloxy)-20(S)-(4-ethyl-4-hydroxyhexylthio)-16α-hydroxypregna-5,7-diene After the same reaction as in Example 56 was conducted using the 20S-isomer from the compounds obtained in Example 53 (61.0 mg, 84.8 μmol), tetrahydrofuran (2.4 ml) and lithium aluminum hydride (5.2 mg, 136 μmol), the residue was purified by preparative thin-layer chromatography (1 plate, hexane:ethyl acetate=3:1, developed 3 times) to give the title compounds β-isomer (40.4 mg, 66%) and α-isomer (12.1 mg, 20%) both as colorless oils.

16β-isomer:

IR(neat): 3450, 2950, 2850, 1460, 1370, 1250, 1100 cm⁻¹.

¹H NMRδ: 0.05(s,6H), 0.06(s,3H), 0.10(s,3H), 0.78–0.94 (m,30H), 3.08–3.22(m,1H), 3.70(brs,1H), 3.97–4.13(m,1H), 4.39–4.52(m,1H), 5.26–5.36(m,1H), 5.55–5.66(m,1H).

MS m/z: 720(M⁺), 73(100%).

UV $\lambda_{max}$ nm: 270, 282, 294.

16α-isomer:

IR(neat): 3440, 2950, 2850, 1460, 1380, 1250, 1100 cm⁻¹.

¹H NMRδ: 0.05(s,3H), 0.06(s,6H), 0.11(s,3H), 0.71(s, 3H), 0.78–0.94(m,27H), 2.81–2.98(m,1H), 3.70(brs,1H), 3.97–4.11(m,1H), 4.15–4.25(m,1H), 5.25–5.33(m,1H), 5.55–5.61(m,1H).

MS m/z: 720(M⁺), 73(100%).

UV $\lambda_{max}$ nm: 270, 281, 293.

EXAMPLE 59

1α,3β-Bis(t-butyldimethylsilyloxy)-20(R)-(4-ethyl-4-hydroxyhexylthio)-16β-hydroxypregna-5,7-diene After the same reaction as in Example 56 was conducted using the 20R-isomer from the compounds obtained in Example 53 (49.9 mg, 69.4 μmol), tetrahydrofuran (2.0 ml) and lithium aluminum hydride (4.2 mg, 111 μmol), the residue was purified by preparative thin-layer chromatography (2 plates, hexane:ethyl acetate=3:1, developed 3 times) to give the title compound as a colorless oil (36.7 mg, 73%).

IR(neat): 3450, 2950, 2850, 1460, 1380, 1250, 1100 cm⁻¹.

¹H NMRδ: 0.05(s,3H), 0.07(s,6H), 0.11(s,3H), 0.78–0.94 (m,30H), 3.06–3.18(m,1H), 3.71(brs,1H), 3.81–3.95(m,1H), 3.98–4.13(m,1H), 5.31–5.39(m,1H), 5.55–5.63(m,1H).

MS m/z: 720(M⁺), 73(100%).

UV $\lambda_{max}$ nm: 270, 282, 293.

EXAMPLE 60

1α,3β-Bis(t-butyldimethylsilyloxy)-20(S)-(4-hydroxy-4-methylpentylthio)-16β-hydroxypregna-5,7-diene and 1α,3β-bis(t-butyldimethylsilyloxy)-20(S)-(4-hydroxy-4-methylpentylthio)-16α-hydroxypregna-5,7-diene After the same reaction as in Example 56 was onducted using the 20S-isomer from the compounds obtained in Example 54 (85.0 mg, 123 μmol), tetrahydrofuran (2.5 ml) and lithium aluminum hydride (7.5 mg, 197 μmol), the residue was purified by preparative thin-layer chromatography (1 plate, hexane:ethyl acetate=1:1, developed 3 times then 1 plate, dichloromethane:ethanol=30:1, developed 5 times) to give the title compounds β-isomer (58.3 mg, 68%) and α-isomer (9.7 mg, 11%) both as colorless oils.

16β-isomer:

IR(neat): 3400, 2950, 2850, 1460, 1380, 1250, 1100 cm⁻¹.

¹H NMRδ: 0.05(s,6H), 0.06(s,3H), 0.10(s,3H), 0.87(s, 9H), 0.88(s,9H), 0.92(s,3H), 0.93(s,3H), 1.25(s,6H), 1.46(d, J=6.3 Hz,3H), 3.07–3.22(m,1H), 3.70(brs,1H), 3.97–4.12 (m,1H), 4.38–4.51(m,1H), 5.25–5.35(m,1H), 5.54–5.66(m, 1H).

MS m/z: 692(M⁺), 73(100%).

UV $\lambda_{max}$ nm: 270, 282, 293.

16α-isomer:

IR(neat): 3420, 2950, 2850, 1460, 1370, 1250, 1090 cm⁻¹.

¹H NMRδ: 0.05(s,3H), 0.06(s,6H), 0.10(s,3H), 0.72(s, 3H), 0.88(s,21H), 1.25(s,6H), 1.48(d,J=6.4 Hz,3H), 2.85–3.03(m,1H), 3.71(brs,1H), 3.96–4.27(m,2H), 5.25–5.34(m,1H), 5.54–5.64(m,1H).

MS m/z: 692(M⁺), 73(100%).

UV $\lambda_{max}$ nm: 270, 282, 293.

EXAMPLE 61

1α,3β-Bis(t-butyldimethylsilyloxy)-20(R)-(4-hydroxy-4-methylpentylthio)-16β-hydroxypregna-5,7-diene After the same synthetic reaction as in Example 56 was conducted using the 20R-isomer from the compounds obtained in Example 54 (91.1 mg, 132 μmol), tetrahydrofuran (2.5 ml) and lithium aluminum hydride (8.0 mg, 211 μmol), the residue was purified by preparative thin-layer chromatography (2 plates, dichloromethane:ethanol=20:1, developed 5 times) to give the title compound as a colorless oil (57.0 mg, 62%).

IR(neat): 3450, 2950, 2850, 1460, 1380, 1250, 1100 cm⁻¹.

¹H NMRδ: 0.05(s,3H), 0.06(s,6H), 0.11(s,3H), 0.72(s, 3H), 0.88(s,18H), 0.92(s,3H), 1.26(s,6H), 1.44(d,J=6.6 Hz,3H), 2.69(t,J=8.0 Hz,2H), 2.97–3.08(m,1H), 3.71(brs, 1H), 3.81–3.94(m,1H), 3.96–4.11(m,1H), 5.30–5.39(m,1H), 5.55–5.62(m,1H).

MS m/z: 692(M⁺), 73(100%).

UV $\lambda_{max}$ nm: 270, 281, 293.

EXAMPLE 62

1α,3β-Bis(t-butyldimethylsilyloxy)-20(S)-(3-ethyl-3-hydroxypentylthio)-16β-hydroxypregna-5,7-diene and 1α,3β-bis(t-butyldimethylsilyloxy)-20(S)-(3-ethyl-3-hydroxypentylthio)-16α-hydroxypregna-5,7-diene After the same synthetic reaction as in Example 56 was conducted using the 20S-isomer from the compounds obtained in Example 55 (98.8 mg, 140 μmol), tetrahydrofuran (5.0 ml) and lithium aluminum hydride (8.5 mg, 224 μmol), the residue was purified by preparative thin-layer chromatography (2 plates, hexane:ethyl acetate=3:1, developed 3 times) to give the title compounds β-isomer (42.6 mg, 43%) and α-isomer (12.2 mg, 12%) both as colorless oils.

16β-isomer:

IR(neat): 3450, 2950, 2850, 1460, 1380, 1260, 1100 cm$^{-1}$.

$^1$H NMRδ: 0.05(s,6H), 0.06(s,3H), 0.10(s,3H), 0.81–0.97(m,30H), 2.60(t,J=8.1 Hz,2H), 3.09–3.25(m,1H), 3.69(brs,1H), 3.94–4.14(m,1H), 4.38–4.51(m,1H), 5.26–5.35(m,1H), 5.55–5.60(m,1H).

MS m/z: 706(M$^+$), 73(100%).

UV λ$_{max}$ nm: 271, 282, 294.

16α-isomer:

IR(neat): 3400, 2950, 2850, 1460, 1370, 1250, 1100 cm$^{-1}$.

$^1$H NMRδ: 0.05(s,3H), 0.06(s,6H), 0.10(s,3H), 0.72(s,3H), 0.80–0.94(m,27H), 2.59(t,J=8.1 Hz,2H), 2.84–2.98(m,1H), 3.69(brs,1H), 3.95–4.10(m,1H), 4.12–4.19(m,1H), 5.25–5.34(m,1H), 5.55–5.63(m,1H).

MS m/z: 706(M$^+$), 73(100%).

UV λ$_{max}$ nm: 270, 281, 293.

EXAMPLE 63

1α,3β-Bis(t-butyldimethylsilyloxy)-20(R)-(3-ethyl-3-hydroxypentylthio)-16β-hydroxypregna-5,7-diene After the same synthetic reaction as in Example 56 was conducted using the 20R-isomer from the compounds obtained in Example 55 (33.3 mg, 47.2 μmol), tetrahydrofuran (1.1 ml) and lithium aluminum hydride (2.9 mg, 75.2 μmol), the residue was purified by preparative thin-layer chromatography (1 plate, hexane:ethyl acetate=3:1, developed 3 times) to give the title compound as a colorless oil (18.2 mg, 55%).

IR(neat): 3430, 2950, 2850, 1460, 1380, 1250, 1100 cm$^{-1}$.

$^1$H NMRδ: 0.05(s,3H), 0.06(s,6H), 0.11(s,3H), 0.78(s,3H), 0.81–0.94(m,27H), 2.64(t,J=8.2 Hz,2H), 3.07–3.19(m,1H), 3.71(brs,1H), 3.82–3.94(m,1H), 3.97–4.11(m,1H), 5.31–5.39(m,1H), 5.55–5.63(m,1H).

MS m/z: 706(M$^+$), 73(100%).

UV λ$_{max}$ nm: 270, 281, 293.

EXAMPLE 64

20(S)-(3-Hydroxy-3-methylbutylthio)-1α,3β,16β-trihydroxypregna-5,7-diene

Under an argon atmosphere, the 16β-isomer from the compounds obtained in Example 56 (70.1 mg, 103 μmol) was dissolved into dry tetrahydrofuran (1.1 ml) and tetra-n-butylammonium fluoride (1M solution in tetrahydrofuran, 1.1 ml) was added, and the mixture was gently refluxed for 16 hours. The mixture was poured into water and extracted with ethyl acetate. The organic layer was washed successively with 10% hydrochloric acid, an aqueous saturated sodium bicarbonate solution and brine, and dried over anhydrous magnesium sulfate. After the solvent was distilled off under reduced pressure, the residue was purified by preparative thin-layer chromatography (1 plate, dichloromethane:ethanol=5:1, developed once) to give the title compound as a colorless oil (41.1 mg, 89%).

IR(neat): 3400, 2950, 1460, 1420, 1380, 1210, 1150, 1050 cm$^{-1}$.

$^1$H NMRδ: 0.93(s,3H), 0.94(s,3H), 1.24(s,6H), 1.46(d,J=6.3 Hz,3H), 2.62(t,J=7.8 Hz,2H), 3.06–3.24(m,1H), 3.73(brs,1H), 3.91–4.10(m,1H), 4.33–4.49(m,1H), 5.30–5.40(m,1H), 5.61–5.71(m,1H).

MS m/z: 450(M$^+$), 69(100%).

UV λ$_{max}$ nm: 271, 282, 293.

EXAMPLE 65

20(S)-(3-Hydroxy-3-methylbutylthio)-1α,3β,16α-trihydroxypregna-5,7-diene

After the same reaction as in Example 64 was conducted using the 16α-isomer from the compounds obtained in Example 56 (22.0 mg, 32.4 μmol), dry tetrahydrofuran (1.1 ml) and tetra-n-butylammonium fluoride (1M solution in tetrahydrofuran, 1.1 ml), the residue was purified by preparative thin-layer chromatography (1 plate, dichloromethane:ethanol=5:1, developed once) to give the title compound as a colorless oil (11.5 mg, 79%).

IR(neat): 3350, 2950, 1450, 1380, 1050 cm$^{-1}$.

$^1$H NMRδ: 0.72(s,3H), 0.93(s,3H), 1.25(s,6H), 1.48(d,J=6.9 Hz,3H), 2.65(t,J=8.1 Hz,2H), 2.85–3.00(m,1H), 3.77(brs,1H), 4.00–4.26(m,2H), 5.31–5.40(m,1H), 5.68–5.76(m,1H).

MS m/z: 450(M$^+$), 69(100%).

UV λ$_{max}$ nm: 270, 282, 293.

EXAMPLE 66

20(R)-(3-Hydroxy-3-methylbutylthio)-1α,3β,16β-trihydroxypregna-5,7-diene

After the same reaction as in Example 64 was conducted using the 16β-isomer from compounds obtained in Example 57 (55.1 mg, 81.1 μmol), dry tetrahydrofuran (1.0 ml) and tetra-n-butylammonium fluoride (1M solution tetrahydrofuran, 1.0 ml), the residue was purified by preparative thin-layer chromatography (1 plate, dichloromethane:ethanol=5:1, developed once) to give the title compound as a colorless oil (31.9 mg, 88%).

IR(neat): 3400, 2950, 1450, 1380, 1210, 1030 cm$^{-1}$.

$^1$H NMRδ: 0.79(s,3H), 0.95(s,3H), 1.24(s,6H), 1.44(d,=6.9 Hz,3H), 2.69(t,J=8.3 Hz,2H), 3.06–3.20(m,1H), 3.76(brs,1H), 3.28–3.95(m,1H), 3.98–4.15(m,1H), 5.37–5.45(m,1H), 5.66–5.75(m,1H).

MS m/z: 450(M$^+$), 69(100%).

UV λ$_{max}$ nm: 270, 281, 293.

EXAMPLE 67

20(R)-(3-Hydroxy-3-methylbutylthio)-1α,3β,16α-trihydroxypregna-5,7-diene

After the same reaction as in Example 64 was conducted using the 16α-isomer from the compounds obtained in Example 57 (15.8 mg, 23.3 μmol), dry tetrahydrofuran (1.0 ml) and tetra-n-butylammonium fluoride (1M solution in tetrahydrofuran, 0.8 ml), the residue was purified by preparative thin-layer chromatography (1 plate, dichloromethane:ethanol=5:1, developed once) to give the title compound as a colorless oil (8.6 mg, 82%).

IR(neat): 3400, 2950, 1450, 1380, 1330, 1210, 1030 cm$^{-1}$.

$^1$H NMRδ: 0.85(s,3H), 0.96(s,3H), 1.26(s,6H), 1.46(d,J=6.6 Hz,3H), 2.70(t,J=7.9 Hz,2H), 3.04–3.19(m,1H), 3.75(brs,1H), 3.97–4.13(m,1H), 4.42–4.53(m,1H), 5.39–5.47(m,1H), 5.71–5.78(m,1H).

MS m/z: 450(M$^+$), 69(100%).

UV λ$_{max}$ nm: 270, 281, 293.

EXAMPLE 68

20(S)-(4-Ethyl-4-hydroxyhexylthio)-1α,3β,16β-trihydroxypregna-5,7-diene

After the same reaction as in Example 64 was conducted using the 16β-isomer from the compounds obtained in Example 58 (36.5 mg, 50.6 μmol), dry tetrahydrofuran (1.0 ml) and tetra-n-butylammonium fluoride (1M solution in tetrahydrofuran, 1.0 ml), the residue was purified by preparative thin-layer chromatography (1 plate, dichloromethane:ethanol=16:3, developed once) to give the title compound as a colorless oil (21.3 mg, 86%).

IR(neat): 3400, 2950, 1460, 1420, 1370, 1250, 1030 cm$^{-1}$.

$^1$H NMRδ: 0.86(t,J=7.3 Hz,6H), 0.93(s,3H), 0.96(s,3H), 3.03–3.23(m,1H), 3.77(brs,1H), 3.96–4.15(m,1H), 4.26–4.52(m,1H), 5.31–5.40(m,1H), 5.67–5.76(m,1H).

MS m/z: 492(M$^+$), 143(100%).

UV λ$_{max}$ nm: 271, 282, 293.

EXAMPLE 69

20(S)-(4-Ethyl-4-hydroxyhexylthio)-1α,3β,16α-trihydroxypregna-5,7-diene

After the same reaction as in Example 64 was conducted using the 16α-isomer from the compounds obtained in Example 58 (12.0 mg, 16.6 μmol), dry tetrahydrofuran (1.0 ml) and tetra-n-butylammonium fluoride (1M solution in tetrahydrofuran, 1.0 ml), the residue was purified by preparative thin-layer chromatography (1 plate, dichloromethane:ethanol=16:3, developed once) to give the title compound as a colorless oil (6.3 mg, 77%).

IR(neat): 3400, 2950, 1450, 1380, 1040 cm$^{-1}$.

$^1$H NMRδ: 0.72(s,3H), 0.86(t,J=7.3 Hz,6H), 0.94(s,3H), 2.80–2.98(m,1H), 3.77(brs,1H), 3.96–4.28(m,2H), 5.29–5.39(m,1H), 5.67–5.75(m,1H).

MS m/z: 492(M$^+$), 143(100%).

UV λ$_{max}$ nm: 271, 282, 293.

EXAMPLE 70

20(R)-(4-Ethyl-4-hydroxyhexylthio)-1α,3β,16β-trihydroxypregna-5,7-diene

After the same reaction as in Example 64 was conducted using the compound obtained in Example 59 (34.0 mg, 47.1 μmol), dry tetrahyteofuran (1.0 ml) and tetra-n-butylammonium fluoride (1M solution in tetrahydrofuran, 1.0 ml), the residue was purified by preparative thin-layer chromatography (1 plate, dichloromethane:ethanol=16:3, developed once) to give the title compound as a colorless oil (12.1 mg, 52%).

IR(neat): 3400, 2950, 1460, 1380, 1040 cm$^{-1}$.

$^1$H NMRδ: 0.80(s,3H), 0.86(t,J=7.3 Hz,6H), 0.97(s,3H), 3.06–3.17(m,1H), 3.78(brs,1H), 3.80–4.06(m,2H), 5.36–5.45(m,1H), 5.67–5.76(m,1H).

MS m/z: 492(M$^+$), 143(100%).

UV λ$_{max}$ nm: 271, 282, 293.

EXAMPLE 71

20(S)-(4-Hydroxy-4-methylpentylthio)-1α,3β,16β-trihydroxypregna-5,7-diene

After the same reaction as in Example 64 was conducted using the 16β-isomer from the compounds obtained in Example 60 (58.3 mg, 84.1 μmol), dry tetrahydrofuran (1.0 ml) and tetra-n-butylammonium fluoride (1M solution in tetrahydrofuran, 1.0 ml), the residue was purified by preparative thin-layer chromatography (1 plate, dichloromethane:ethanol=5:1, developed once) to give the title compound as a colorless oil (22.9 mg, 59%).

IR(neat): 3400, 2950, 1450, 1380, 1050 cm$^{-1}$.

$^1$H NMRδ: 0.94(s,3H), 0.97(s,3H), 1.23(s,6H), 1.47(d,J=6.3 Hz,3H), 3.07–3.22(m,1H), 3.78(brs,1H), 4.00–4.16(m,1H), 4.40–4.52(m,1H), 5.34–5.41(m,1H), 5.69–5.76(m,1H).

MS m/z: 464(M$^+$), 117(100%).

UV λ$_{max}$ nm: 270, 282, 293.

EXAMPLE 72

20(S)-(4-Hydroxy-4-methylpentylthio)--1α,3β,16α-trihydroxypregna-5,7-diene

After the same reaction as in Example 64 was conducted using the 16α-isomer from the compounds obtained in Example 60 (9.7 mg, 14.0 μmol), dry tetrahydrofuran (1.0 ml) and tetra-n-butylammonium fluoride (1M solution in tetrahydrofuran, 1.0 ml), the residue was purified by preparative thin-layer chromatography (1 plate, dichloromethane:ethanol=5:1, developed once) to give the title compound as a colorless oil (4.6 mg, 71%).

IR(neat): 3400, 2950, 1450, 1380, 1040 cm$^{-1}$.

$^1$H NMRδ: 0.72(s,3H), 0.94(s,3H), 1.22(s,6H), 1.46(d,J=6.6 Hz,3H), 2.83–2.98(m,1H), 3.77(brs,1H), 4.00–4.13(m,1H), 4.16–4.24(m,1H), 5.32–5.39(m,1H), 5.68–5.75(m,1H).

MS m/z: 464(M$^+$), 117(100%).

UV λ$_{max}$ nm: 270, 282, 293.

EXAMPLE 73

20(R)-(4-Hydroxy-4-methylpentylthio)-1α,3β,16β-trihydroxypregna-5,7-diene

After the same reaction as in Example 64 was conducted using the compound obtained in Example 61 (57.0 mg, 82.2 μmol), dry tetrahydrofuran (1.0 ml) and tetra-n-butylammonium fluoride (1M solution in tetrahydrofuran, 1.0 ml), the residue was purified by preparative thin-layer chromatography (1 plate, dichloromethane:ethanol=5:1, developed once) to give the title compound as a colorless oil (30.4 mg, 80%).

IR(neat): 3400, 2950, 1450, 1380, 1220, 1040 cm$^{-1}$.

$^1$H NMRδ: 0.80(s,3H), 0.96(s,3H), 1.22(s,6H), 1.42(d,J=6.9 Hz,3H), 3.05–3.18(m,1H), 3.77(brs,1H), 3.80–3.96(m,1H), 3.98–4.16(m,1H), 5.38–5.47(m,1H), 5.68–5.75(m,1H).

MS m/z: 464(M$^+$), 117(100%).

UV λ$_{max}$ nm: 270, 282, 293.

EXAMPLE 74

20(S)-(3-Ethyl-3-hydroxypentylthio)-1α,3β,16β-trihydroxypregna-5,7-diene

After the same reaction as in Example 64 was conducted using the 16β-isomer from the compounds obtained in Example 62 (42.6 mg, 60.2 μmol), dry tetrahydrofuran (1.0 ml) and tetra-n-butylammonium fluoride (1M solution in tetrahydrofuran, 1.2 ml), the residue was purified by preparative thin-layer chromatography (1 plate, dichloromethane:ethanol=5:1, developed once) to give the title compound as a colorless oil (23.9 mg, 83%).

IR(neat): 3400, 2950, 1460, 1380, 1330, 1260, 1050 cm$^{-1}$.

$^1$H NMRδ: 0.87(t,J=7.3 Hz,6H), 0.93(s,3H), 0.95(s,3H), 2.59(t,J=8.2 Hz,2H), 3.03–3.24(m,1H), 3.75(brs,1H), 3.93–4.13(m,1H), 4.33–4.51(m,1H), 5.28–5.40(m,1H), 5.65–5.74(m,1H).

MS m/z: 478(M$^+$), 87(100%).

UV λ$_{max}$ nm: 271, 282, 294.

EXAMPLE 75

20(S)-(3-Ethyl-3-hydroxypentylthio)-1α,3β,16α-trihydroxypregna-5,7-diene

After the same reaction as in Example 64 was conducted using the 16α-isomer from the compounds obtained in Example 62 (12.2 mg, 17.2 μmol), dry tetrahydrofuran (1.0 ml) and tetra-n-butylammonium fluoride (1M solution in tetrahydrofuran, 1.0 ml), the residue was purified by preparative thin-layer chromatography (1 plate, dichloromethane:ethanol=5:1, developed once) to give the title compound as a colorless oil (6.3 mg, 77%).

IR(neat): 3400, 2950, 1460, 1380, 1330, 1220, 1040 cm$^{-1}$.

$^1$H NMRδ: 0.72(s,3H), 0.87(t,J=7.3 Hz,6H), 0.93(s,3H), 2.59(t,J=7.9 Hz,2H), 2.84–2.99(m,1H), 3.77(brs,1H), 3.96–4.24(m,2H), 5.31–5.40(m,1H), 5.67–5.76(m,1H).

MS m/z: 478(M$^+$), 87(100%).

UV λ$_{max}$ nm: 271, 282, 293.

EXAMPLE 76

20(R)-(3-Ethyl-3-hydroxypentylthio)-1α,3β,16β-trihydroxypregna-5,7-diene

After the same reaction as in Example 64 was conducted using the compound obtained in Example 63 (18.0 mg, 25.5 μmol), dry tetrahydrofuran (1.0 ml) and tetra-n-butylammonium fluoride (1M solution in tetrahydrofuran, 1.0 ml), the residue was purified by preparative thin-layer chromatography (1 plate, dichloromethane:ethanol=5:1, developed once) to give the title compound as a colorless oil (8.5 mg, 70%).

IR(neat): 3400, 2950, 1460, 1380, 1280, 1030 cm$^{-1}$.

$^1$H NMRδ: 0.80(s,3H), 0.87(t,J=7.3 Hz,6H), 0.97(s,3H), 2.64(t,J=8.3 Hz,2H), 3.07–3.18(m,1H), 3.78(brs,1H), 3.83–3.96(m,1H), 3.99–4.15(m,1H), 5.40–5.48(m,1H), 5.69–5.77(m,1H).

MS m/z: 478(M$^+$), 87(100%).

UV λ$_{max}$ nm: 270, 281, 293.

EXAMPLE 77

20(S)-(3-Hydroxy-3-methylbutylthio)-1α,3β,16β-trihydroxy-9,10-secopregna-5,7,10(19)-triene The compound obtained in Example 64 (40.2 mg, 89.2 μmol) was dissolved into ethanol (200 ml) and irradiated using a 400 W high-pressure mercury lamp with a Vycor filter for 2.5 minutes under bubbling with argon at 0° C., and then gently refluxed for 2 hours. The solvent was distilled off and the residue was purified by preparative thin-layer chromatography (1 plate, dichloromethane:ethanol=5:1, developed 3 times) to give the title compound as a colorless oil (4.6 mg, 11%).

IR(neat): 3400, 2950, 1450, 1370, 1200, 1050 cm$^{-1}$.

$^1$H NMRδ: 0.84(s,3H), 1.25(s,6H), 1.47(d,J=6.3 Hz,3H), 2.64(t,J=7.9 Hz,2H), 3.05–3.24(m,1H), 4.16–4.29(br,1H), 4.34–4.49(br,2H), 5.00(s,1H), 5.33(s,1H), 6.02(d,J=11.6 Hz,1H), 6.36(d,J=11.6 Hz,1H).

MS m/z: 450(M$^+$), 69(100%).

UV λ$_{max}$ nm: 263, λ$_{min}$ nm: 227.

EXAMPLE 78

20(S)-(3-Hydroxy-3-methylbutylthio)-1α,3β,16α-trihydroxy-9,10-secopregna-5,7,10(19)-triene After the same reaction as in Example 77 (irradiation for 2.5 minutes) was conducted using the compound obtained in Example 65 (11.5 mg, 25.5 μmol), the residue was purified by preparative thin-layer chromatography (1 plate, dichloromethane:ethanol=6:1, developed 5 times) to give the title compound as a colorless oil (0.7 mg, 6%).

IR(neat): 3350, 2950, 1450, 1380, 1200, 1050 cm$^{-1}$.

$^1$H NMRδ: 0.64(s,3H), 1.25(s,6H), 1.46(d,J=6.9 Hz,3H), 2.64(t,J=7.9 Hz,2H), 2.82–2.97(m,1H), 4.10–4.30(br,2H), 4.40–4.51(br,1H), 4.99(s,1H), 5.33(s,1H), 5.96(d,J=11.1 Hz,1H), 6.37(d,J=11.1 Hz,1H).

MS m/z: 450(M$^+$), 69(100%).

UV λ$_{max}$ nm: 263, λ$_{min}$ nm: 227.

EXAMPLE 79

20(R)-(3-Hydroxy-3-methylbutylthio)-1α,3β,16β-trihydroxy-9,10-secopregna-5,7,10(19)-triene After the same reaction as in Example 77 (irradiation for 2.5 minutes) was conducted using the compound obtained in Example 66 (31.9 mg, 70.8 μmol), the residue was purified by preparative thin-layer chromatography (1 plate, dichloromethane:ethanol=6:1, developed twice) to give the title compound as a colorless oil (3.5 mg, 11%).

IR(neat): 3350, 2950, 1450, 1380, 1210, 1060 cm$^{-1}$.

$^1$H NMRδ: 0.71(s,3H), 1.25(s,6H), 1.44(d,J=6.6 Hz,3H), 2.70(t,J=7.9 Hz,2H), 3.04–3.20(m,1H), 3.84–3.97(br,1H), 4.16–4.35(br,1H), 4.37–4.50(br,1H), 5.00(s,1H), 5.34(s,1H), 5.97(d,J=11.7 Hz,1H), 6.36(d,J=11.7 Hz,1H).

MS m/z: 450(M$^+$), 69(100%).

UV λ$_{max}$ nm: 263, λ$_{min}$ nm: 227.

EXAMPLE 80

20(R)-(3-Hydroxy-3-methylbutylthio)-1α,3β,16α-trihydroxy-9,10-secopregna-5,7,10(19)-triene After the same reaction as in Example 77 (irradiation for 2.0 minutes) was conducted using the compound obtained in Example 67 (8.6 mg, 19.1 μmol), the residue was purified by preparative thin-layer chromatography (1 plate, dichloromethane:ethanol=6:1, developed 5 times) to give the title compound as a colorless oil (1.3 mg, 15%).

IR(neat): 3400, 2950, 1460, 1380, 1200, 1060 cm$^{-1}$.

$^1$H NMRδ: 0.76(s,3H), 1.26(s,6H), 1.44(d,J=6.6 Hz,3H), 2.70(t,J=8.1 Hz,2H), 3.00–3.16(m,1H), 4.18–4.31(br,1H), 4.37–4.51(br,2H), 5.00(s,1H), 5.31(s,1H), 6.07(d,J=11.2 Hz,1H), 6.36(d,J=11.2 Hz,1H).

MS m/z: 450(M$^+$), 69(100%).

UV λ$_{max}$ nm: 262, λ$_{min}$ nm: 227.

EXAMPLE 81

20(S)-(4-Ethyl-4-hydroxyhexylthio)-1α,3β,16β-trihydroxy-9,10-secopregna-5,7,10(19)-triene After the same reaction as in Example 77 (irradiation for 2.5 minutes) was conducted using the compound obtained in Example 68 (21.3 mg, 43.2 μmol), the residue was purified by preparative thin-layer chromatography (1 plate, dichloromethane:ethanol=10:1, developed 3 times) to give the title compound as a colorless oil (3.9 mg, 18%).

IR(neat): 3400, 2930, 1450, 1380, 1050 cm$^{-1}$.

$^1$H NMRδ: 0.67–0.90(m,9H), 3.03–3.19(m,1H), 4.16–4.28(br,1H), 4.34–4.50(br,2H), 5.01(s,1H), 5.33(s,1H), 6.02(d,J=11.2 Hz,1H), 6.37(d,J=11.2 Hz,1H).

MS m/z: 492(M$^+$), 69(100%).

UV λ$_{max}$ nm: 262, λ$_{min}$ nm: 227.

EXAMPLE 82

20(S)-(4-Ethyl-4-hydroxyhexylthio)-1α,3β,16α-trihydroxy-9,10-secopregna-5,7,10(19)-triene After the same reaction as in Example 77 (irradiation for 1.75 minutes) was conducted using the compound obtained in Example 69 (6.3 mg, 12.7 μmol), the residue was purified by preparative thin-layer chromatography (1 plate, dichloromethane:ethanol=10:1, developed 5 times) to give the title compound as a colorless oil (1.3 mg, 21%).

IR(neat): 3400, 2930, 1460, 1380, 1050 cm$^{-1}$.

$^1$H NMRδ: 0.64(s,3H), 0.86(t,J=7.3 Hz,6H), 2.79–2.96 (m,1H), 4.07–4.30(m,2H), 4.39–4.50(br,1H), 4.99(s,1H), 5.33(s,1H), 5.96(d,J=11.2 Hz,1H), 6.37(d,J=11.2 Hz,1H).

MS m/z: 492(M$^+$), 69(100%).

UV λ$_{max}$ nm: 262, λ$_{min}$ nm: 227.

EXAMPLE 83

20(R)-(4-Ethyl-4-hydroxyhexylthio)-1α,3β,16β-trihydroxy-9,10-secopregna-5,7,10(19)-triene After the same reaction as in Example 77 (irradiation for 1.75 minutes) was conducted using the compound obtained in Example 70 (12.1 mg, 24.6 μmol), the residue was purified by preparative thin-layer chromatography (1 plate, dichloromethane:ethanol=10:1, developed 3 times) to give the title compound as a colorless oil (1.5 mg, 12%).

IR(neat): 3400, 2930, 1460, 1380, 1050 cm$^{-1}$.

$^1$H NMRδ: 0.72(s,3H), 0.86(t,J=7.3 Hz,6H), 3.04–3.20 (m,1H), 3.81–3.97(m,1H), 4.26–4.31(br,1H), 4.38–4.50(br, 1H), 5.01(s,1H), 5.35(s,1H), 5.97(d,J=11.2 Hz,1H), 6.36(d,J=11.2 Hz,1H).

MS m/z: 492(M$^+$), 69(100%).

UV λ$_{max}$ nm: 262, λ$_{min}$ nm: 227.

EXAMPLE 84

20(S)-(4-Hydroxy-4-methylpentylthio)-1α,3β,16β-trihydroxy-9,10-secopregna-5,7,10(19)-triene After the same reaction as in Example 77 (irradiation for 2.5 minutes) was conducted using the compound obtained in Example 71 (22.9 mg, 49.2 μmol), the residue was purified by preparative thin-layer chromatography (1 plate, dichloromethane:ethanol=10:1, developed 7 times) to give the title compound as a colorless oil (2.4 mg, 10%).

IR(neat): 3400, 2930, 1450, 1370, 1200, 1050 cm$^{-1}$.

$^1$H NMRδ: 0.84(s,3H), 1.22(s,6H), 1.46(d,J=6.1 Hz,3H), 3.00–3.20(m,1H), 4.16–4.29(br,1H), 4.34–4.50(br,2H), 5.01 (s,1H), 5.33(s,1H), 6.01(d,J=11.2 Hz,1H), 6.37(d,J=11.2 Hz,1H).

MS m/z: 464(M$^+$), 117(100%).

UV λ$_{max}$ nm: 263, λ$_{min}$ nm: 227.

EXAMPLE 85

20(S)-(4-Hydroxy-4-methylpentylthio)--1α,3β,16α-trihydroxy-9,10-secopregna-5,7,10(19)-triene After the same reaction as in Example 77 (irradiation for 1.25 minutes) was conducted using the compound obtained in Example 72 (5.9 mg, 12.7 μmol), the residue was purified by preparative thin-layer chromatography (1 plate, dichloromethane:ethanol=10:1, developed 5 times) to give the title compound as a colorless oil (0.5 mg, 8%).

IR(neat): 3350, 2920, 1450, 1370, 1260, 1050 cm$^{-1}$.

$^1$H NMRδ: 0.64(s,3H), 1.22(s,6H), 1.45(d,J=6.6 Hz,3H), 2.79–2.92(m,1H), 4.40–4.34(br,2H), 4.37–4.50(br,1H), 4.99 (s,1H), 5.33(s,1H), 5.95(d,J=11.2 Hz,1H), 6.35(d,J=11.2 Hz,1H).

MS m/z: 464(M$^+$), 117(100%).

UV λ$_{max}$ nm: 262, λ$_{min}$ nm: 227.

EXAMPLE 86

20(R)-(4-Hydroxy-4-methylpentylthio)-1α,3β,16β-trihydroxy-9,10-secopregna-5,7,10(19)-triene After the same reaction as in Example 77 (irradiation for 2.25 minutes) was conducted using the compound obtained in Example 73 (18.3 mg, 39.4 μmol), the residue was purified by preparative thin-layer chromatography (1 plate, dichloromethane:ethanol=10:1, developed 5 times) to give the title compound as a colorless oil (1.5 mg, 8%).

IR(neat): 3400, 2920, 1450, 1380, 1260, 1050 cm$^{-1}$.

$^1$H NMRδ: 0.72(s,3H), 1.22(s,6H), 1.42(d,J=6.9 Hz,3H), 3.04–3.17(m,1H), 3.84–3.97(m,1H), 4.19–4.31(br,1H), 4.38–4.50(br,1H), 5.01(s,1H), 5.34(s,1H), 6.00(d,J=11.2 Hz,1H), 6.37(d,J=11.2 Hz,1H).

MS m/z: 464(M$^+$), 117(100%).

UV λ$_{max}$ nm: 262, λ$_{min}$ nm: 227.

EXAMPLE 87

20(S)-(3-Ethyl-3-hydroxypentylthio)-1α,3β,16β-trihydroxy-9,10-secopregna-5,7,10(19)-triene After the same reaction as in Example 77 (irradiation for 2.5 minutes) was conducted using the compound obtained in Example 74 (23.9 mg, 49.9 μmol), the residue was purified by preparative thin-layer chromatography (1 plate, dichloromethane:ethanol=10:1, developed 6 times) to give the title compound as a colorless oil (4.3 mg, 18%).

IR(neat): 3400, 2930, 1450, 1380, 1050 cm$^{-1}$.

$^1$H NMRδ: 0.84(s,3H), 0.87(t,J=7.3 Hz,6H), 2.59(t,J=8.3 Hz,2H), 3.06–3.22(m,1H), 4.18–4.31(br,1H), 4.34–4.50(br, 2H), 5.01(s,1H), 5.33(s,1H), 6.02(d,J=11.2 Hz,1H), 6.37(d, J=11.2 Hz,1H).

MS m/z: 478(M$^+$), 131(100%).

UV λ$_{max}$ nm: 263, λ$_{min}$ nm: 227.

EXAMPLE 88

20(S)-(3-Ethyl-3-hydroxypentylthio)-1α,3β,16α-trihydroxy-9,10-secopregna-5,7,10(19)-triene After the same reaction as in Example 77 (irradiation for 1.5 minutes) was conducted using the compound obtained in Example 75 (6.3 mg, 13.2 μmol), the residue was purified by preparative thin-layer chromatography (1 plate, dichloromethane:ethanol=10:1, developed 8 times) to give the title compound as a colorless oil (1.0 mg, 18%).

IR(neat): 3400, 2950, 1450, 1380, 1050 cm$^{-1}$.

$^1$H NMRδ: 0.64(s,3H), 0.87(t,J=7.3 Hz,6H), 2.59(t,J=7.9 Hz,2H), 2.83–2.98(m,1H), 4.07–4.31(m,2H), 4.39–4.49(br, 1H), 4.99(s,1H), 5.34(s,1H), 5.96(d,J=11.2 Hz,1H), 6.37(d, J=11.2 Hz,1H).

MS m/z: 478(M$^+$), 131(100%).

UV λ$_{max}$ nm: 263, λ$_{min}$ nm: 227.

EXAMPLE 89

20(R)-(3-Ethyl-3-hydroxypentylthio)-1α,3β,16β-trihydroxy-9,10-secopregna-5,7,10(19)-triene After the same reaction as in Example 77 (irradiation for 1.75 minutes) was conducted using the compound obtained in Example 76 (8.5 mg, 17.8 μmol), the residue was purified by preparative thin-layer chromatography (1 plate, dichloromethane:ethanol=10:1, developed 8 times) to give the title compound as a colorless oil (1.1 mg, 13%).

IR(neat): 3400, 2920, 1450, 1380, 1140, 1050 cm$^{-1}$.

$^1$H NMRδ: 0.71(s,3H), 0.87(t,J=7.3 Hz,6H), 2.65(t,J=8.2 Hz,2H), 3.08–3.17(m,1H), 3.84–3.97(m,1H), 4.18–4.31(m,1H), 4.40–4.50(br,1H), 5.01(s,1H), 5.34(s,1H), 5.98(d,J=11.2 Hz,1H), 6.36(d,J=11.2 Hz,1H).

MS m/z: 478(M$^+$), 131(100%).

UV λ$_{max}$ nm: 262, λ$_{min}$ nm: 227.

Test Example 1

Experiment on Inhibition of Proliferation of Human Keratinocytes

1) Human keratinocytes were plated at 2.4×10$^3$ cells/well (0.32 cm$^2$) onto a 96-well plate on which J2 cells treated with X-rays had previously been plated, and then the plate was incubated with the test compound at each concentration on KGM/DMEM (1:1) medium for 3 days at 37° C. in 5% CO$_2$, 95% air.

2) [$^3$H] Thymidine was added at a final concentration of 1 μCi/ml and the plate was incubated for further 3 days.

Figure 2:
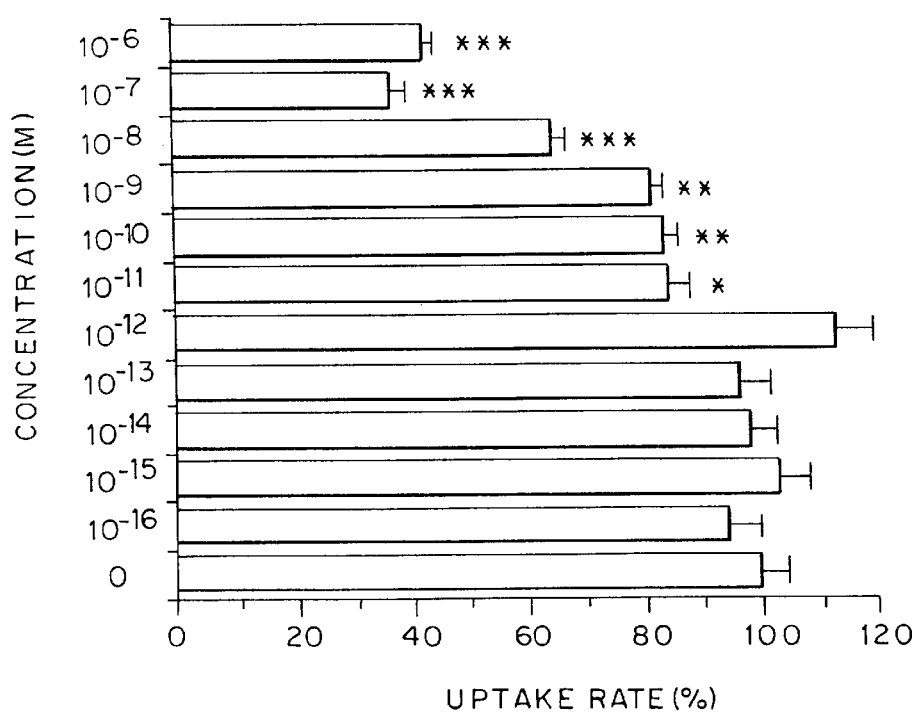
FIG. 2 is a graph showing an inhibitory effect against proliferation of human keratinocytes at each concentration of the compound of Example 88.

3) After the plate was washed with PBS twice, cells were stripped off with 0.25% trypsin and the amount of [$^3$H] thymidine taken into DNA was measured by Betaplate (Pharmacia). The uptake rate at each concentration of the test compound is plotted against 100% corresponding to the [$^3$H] thymidine uptake in the absence of the test compound. FIGS. 1 and 2 show the results of 1α,25-dihydroxyvitamin D$_3$ and the compound obtained in Example 88, respectively.

Test Example 2

1) Human keratinocytes were plated at 2.2×10$^3$ cells/well (0.32 cm$^2$) onto a 96-well plate, and then the plate was incubated with the test compound at each concentration on KGM/DMEM (1:1) medium for one day at 37° C. in 5% CO$_2$, 95% air.

2) [$^3$H] Thymidine was added at a final concentration of 1 μCi/ml and the plate was incubated for further 3 days.

Figure 3:
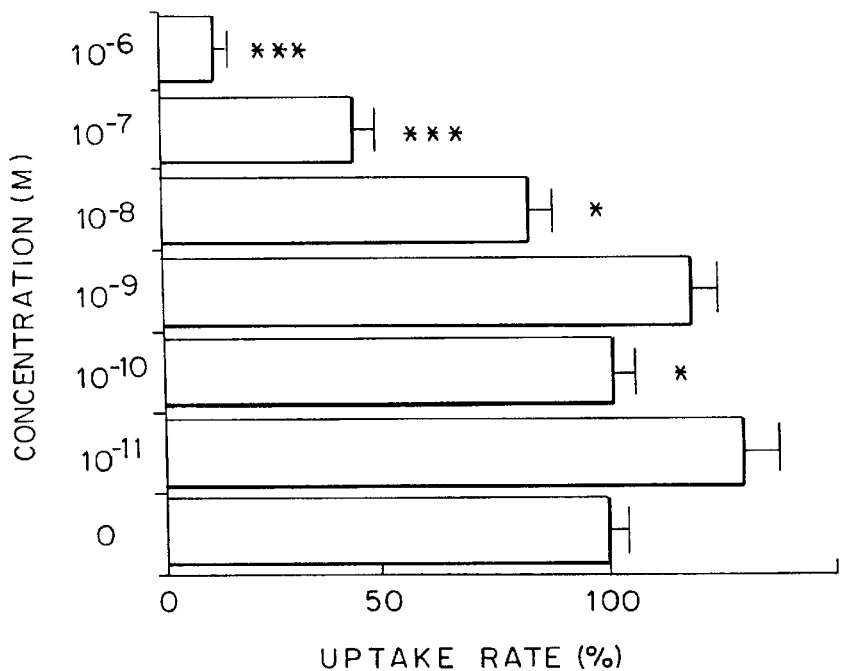
FIG. 3 is a graph showing an inhibitory effect against proliferation of human keratinocytes at each concentration of 1α,25-dihydroxyvitamin $D_3$.
Figure 4:
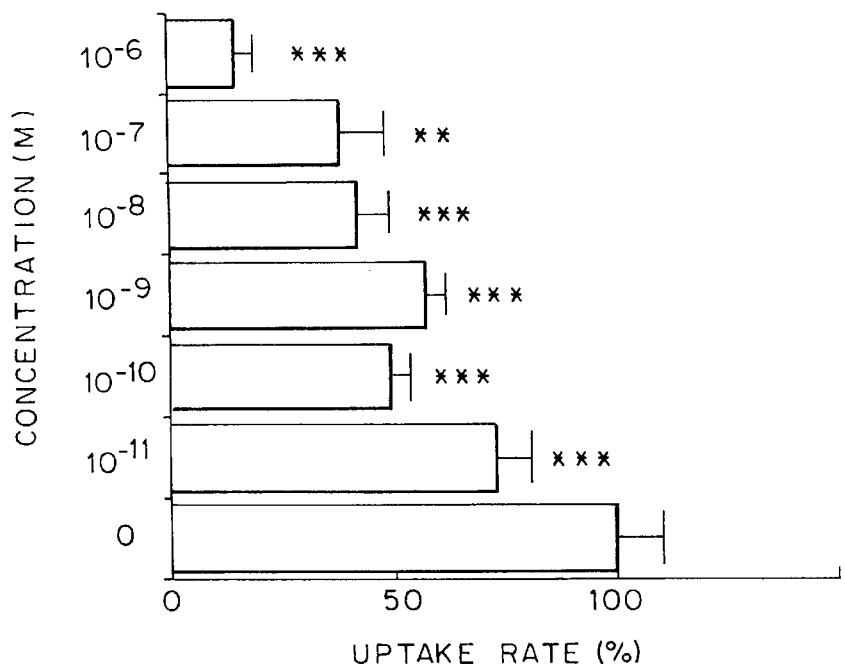
FIG. 4 is a graph showing an inhibitory effect against proliferation of human keratinocytes at each concentration of the compound of Example 33.
Figure 5:
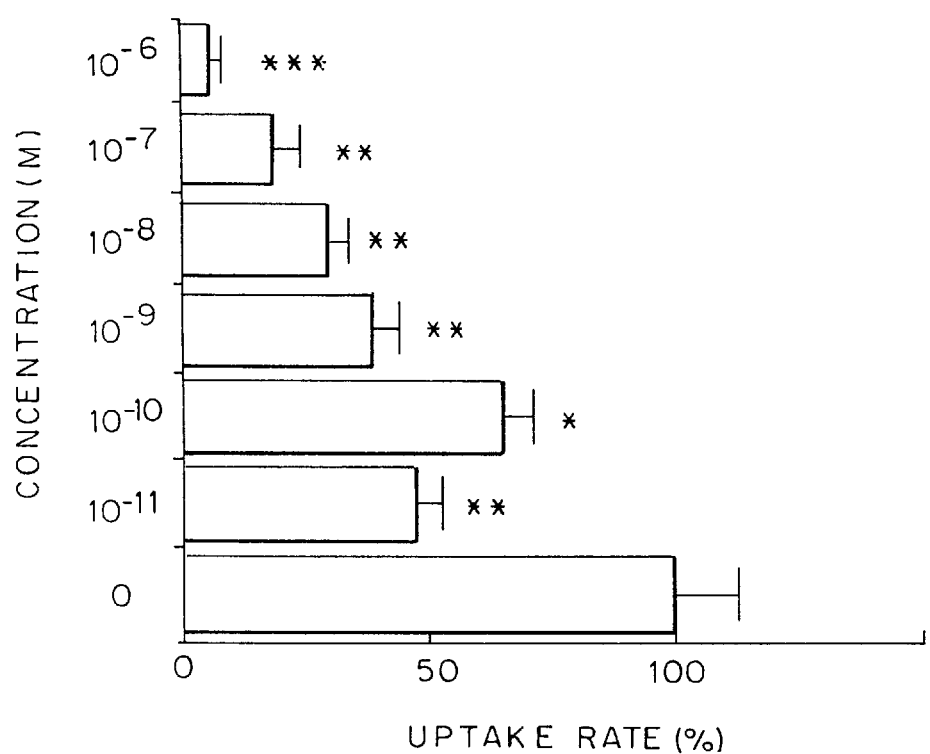
FIG. 5 is a graph showing an inhibitory effect against proliferation of human keratinocytes at each concentration of the compound of Example 35.

3) After the plate was washed with PBS twice, cells were stripped off with 0.25% trypsin and the amount of [$^3$H] thymidine taken into DNA was measured by Betaplate (Pharmacia). The uptake rate at each concentration of the test compound is plotted against 100% corresponding to the [$^3$H] thymidine uptake in the absence of the test compound. FIGS. 3, 4 and 5 show the results of 1α,25-dihydroxyvitamin D$_3$, the compound obtained in Example 33 and the compound obtained in Example 35, respectively.

In the graphs of FIGS. 1 to 5, ★, ★★ and ★★★ mean significant differences at probabilities of 5%, 1% and 0.1%, respectively. As evident from FIGS. 1 to 5, the compounds of this invention have a strong inhibitory effect against proliferation of human keratinocytes.

INDUSTRIAL APPLICABILITY

The compounds of this invention, vitamin D$_3$ derivatives substituted by sulfur atoms at the 22-position have a strong inhibitory effect against proliferation of keratinocytes.

We claim:
1. A compound of the general formula (I):

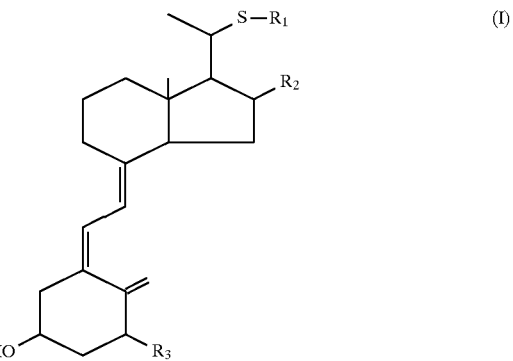

wherein R$_1$ represents a C1-10 alkyl group which may be substituted by one or more hydroxyl groups provided that the terminal carbon atom of R$_1$ group is a primary carbon atom or a secondary carbon atom, or R$_1$ is an unsubstituted alkyl group or an alkyl group substituted by 2 or more hydroxyl groups, R$_2$ represents a hydrogen atom or a hydroxyl group, and R$_3$ represents a hydrogen atom or a hydroxyl group.

2. A compound according to claim 1 wherein R$_3$ is a hydroxyl group.

3. A compound according to claim 2 wherein R$_1$ is a C1-10 alkyl group substituted by two or more hydroxyl groups.

4. A compound according to claim 1 of the general formula (II):

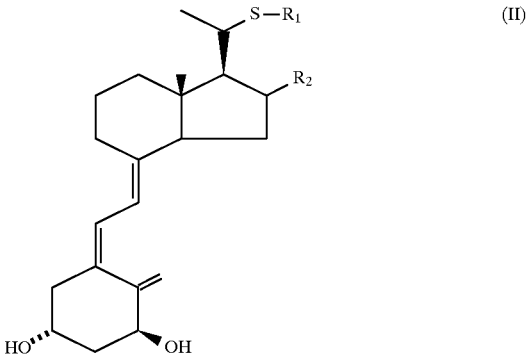

wherein R$_1$ represents a C1-10 alkyl group which may be substituted by one or more hydroxyl groups provided that the terminal carbon atom of R$_1$ group is a primary carbon atom or a secondary carbon atom, or R$_1$ is an unsubstituted alkyl group or an alkyl group substituted by 2 or more hydroxyl groups, and R$_2$ represents a hydrogen atom or a hydroxyl group.

5. A compound according to claim 4 wherein R$_1$ is a C1-10 alkyl group substituted by two or more hydroxyl groups.

6. A compound according to claim 5 wherein R$_1$ is a group of the general formula (III):

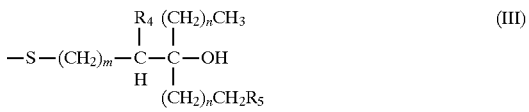

wherein R$_4$ and R$_5$, which may be the same or different, each represents a hydrogen atom or a hydroxyl group provided that the both are not hydroxyl groups, m represents an integer of 1 through 4, and n represents an integer of 0 through 2.

7. A compound according to claim 1 wherein $R_2$ is a hydrogen atom.

8. A compound according to claim 6 wherein $R_2$ is a hydrogen atom.

9. A compound according to claim 6 wherein the 20-position is in R-configuration.

10. A compound according to claim 6 wherein the 20-position is in S-configuration.

11. A compound of the general formula (I):

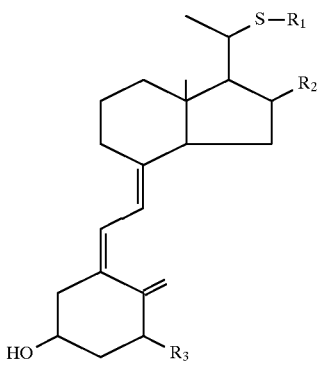

wherein $R_1$ represents a C1-10 alkyl group which may be substituted by one or more hydroxyl groups, $R_2$ represents a hydroxyl group, and $R_3$ represents a hydrogen atom or a hydroxyl group.

12. A compound according to claim 11 wherein $R_3$ is a hydroxyl group.

13. A compound according to claim 11 wherein $R_1$ is a $C_{1-10}$ alkyl group substituted by one or more hydroxyl groups.

14. A compound according to claim 11 of the general formula (II):

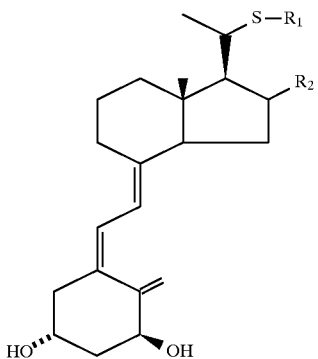

wherein $R_1$ represents a $C_{1-10}$ alkyl group which may be substituted by one or more hydroxyl groups, and $R_2$ represents a hydrogen atom or a hydroxyl group.

15. A compound according to claim 11 wherein $R_1$ is a $C_{1-10}$ alkyl group substituted by one or more hydroxyl groups.

16. A compound according to claim 11 wherein the 20-position is in R-configuration.

17. A compound according to claim 11 wherein the 20-position is in S-configuration.

18. A compound according to claim 11 wherein $R_1$ is a group of the general formula (III):

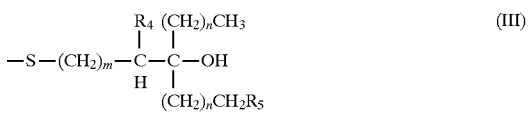

wherein $R_4$ and $R_5$, which may be the same or different, each represents a hydrogen atom or a hydroxyl group provided that the both are not hydroxyl groups, m represents an integer of 1 through 4, and n represents an integer of 0 through 2.

19. A compound according to claim 18 wherein the 20-position is in R-configuration.

20. A compound according to claim 18 wherein the 20-position is in S-configuration.

21. A compound according to claim 18 wherein the $R_4$ and $R_5$ are hydrogen atoms.

22. A compound of the formula (I):

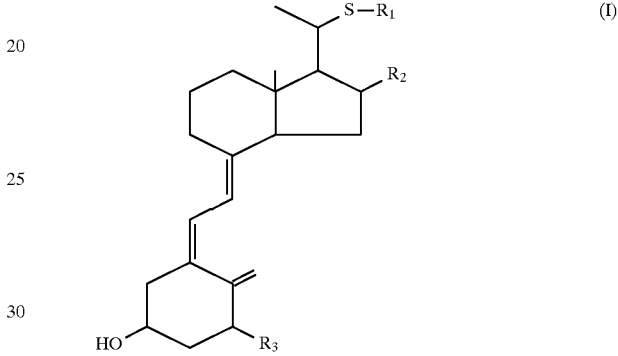

wherein $R_2$ represents a hydrogen atom or a hydroxyl group, $R_3$ represents a hydrogen atom or a hydroxyl group, and $R_1$ is a straight chain $C_{1-10}$ alkyl group which may be substituted by one or more hydroxyl groups, a branched chain $C_{1-10}$ alkyl group which may be substituted by two or more hydroxyl groups, or a group of the formula (III):

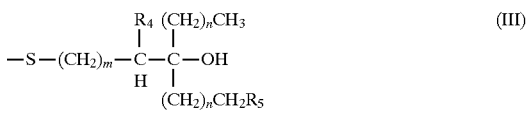

wherein $R_4$ represents a hydroxyl group and $R_5$ represents a hydrogen atom, m represents an integer of 1 through 4, and n represents an integer of 0 through 2.

23. A compound of the formula (I):

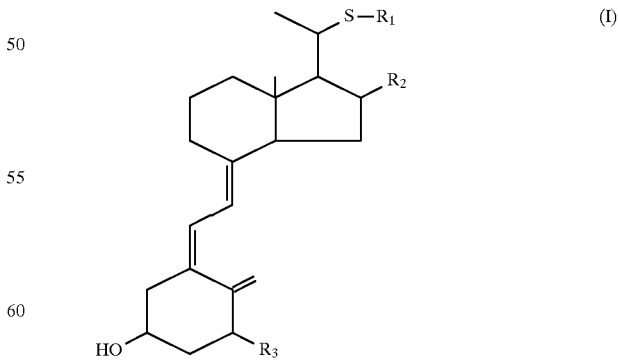

wherein $R_2$ represents a hydrogen atom or a hydroxyl group, $R_3$ represents a hydrogen atom or a hydroxyl group, and $R_1$ is selected from the group consisting of 3-hydroxy-3-methylbutyl, 2-hydroxy-3-methylbutyl, 4-hydroxy-3-methylbutyl, 2,3-dihydroxy-3-methylbutyl, 2,4-dihydroxy- 3-methylbutyl, 3,4-dihydroxy-3-methylbutyl, 3-hydroxy-3-ethylpentyl, 2-hydroxy-3-ethylpentyl, 4-hydroxy-3-ethylpentyl, 2,3-dihydroxy-3-ethylpentyl, 2,4-dihydroxy-3-ethylpentyl, 3,4-dihydroxy-3-ethylpentyl, 4-hydroxy-4-methylpentyl, 3-hydroxy-4-methylpentyl, 5-hydroxy-4-methylpentyl, 3,4-dihydroxy-4-methylpentyl, 3,5-dihydroxy-4-methylpentyl, 4,5-dihydroxy-4-methylpentyl, 3-hydroxy-3-(n-propyl)hexyl, 4-hydroxy-3-(n-propyl)hexyl, 2-hydroxy-3-(n-propyl)hexyl, 2,3-dihydroxy-3-(n-propyl)hexyl, 3,4-dihydroxy-3-(n-propyl)hexyl, 2,4-dihydroxy-3-(n-propyl)hexyl, 3-hydroxy-4-ethylhexyl, 4-hydroxy-4-ethylhexyl, 5-hydroxy-4-ethylhexyl, 3,4-dihydroxy-4-ethylhexyl, 3,5-dihydroxy-4-ethylhexyl, 4,5-dihydroxy-4-ethylhexyl, 4-hydroxy-5-methylhexyl, 5-hydroxy-5-methylhexyl, 6-hydroxy-5-methylhexyl, 4,5-dihydroxy-5-methylhexyl, 4,6-dihydroxy-5-methylhexyl, 5,6-dihydroxy-5-methylhexyl, 5-hydroxy-6-methylheptyl, 6-hydroxy-6-methylheptyl, 7-hydroxy-6-methylheptyl, 5,6-dihydroxy-6-methylheptyl, 5,7-dihydroxy-6-methylheptyl, 6,7-dihydroxy-6-methylheptyl, 4-hydroxy-5-ethylheptyl, 5-hydroxy-5-ethylheptyl, 6-hydroxy-5-ethylheptyl, 4,5-dihydroxy-5-ethylheptyl, 4,6-dihydroxy-5-ethylheptyl, 5,6-dihydroxy-5-ethylheptyl, 3-hydroxy-4-(n-propyl)heptyl, 4-hydroxy-4-(n-propyl)heptyl, 5-hydroxy-4-(n-propyl)heptyl, 3,4-dihydroxy-4-(n-propyl)heptyl, 3,5-dihydroxy-4-(n-propyl)heptyl and 4,5-dihydroxy-4-(n-propyl)heptyl groups, preferably 3-hydroxy-3-methylbutyl, 2,3-dihydroxy-3-methylbutyl, 3,4-dihydroxy-3-methylbutyl, 3-hydroxy-3-ethylpentyl, 2,3-dihydroxy-3-ethylpentyl, 3,4-dihydroxy-3-ethylpentyl, 4-hydroxy-4-methylpentyl, 3,4-dihydroxy-4-methylpentyl and 4,5-dihydroxy-4-methylpentyl.

24. A compound according to claim 23 wherein $R_1$ is selected from the group consisting of 3-hydroxy-3-methylbutyl, 3-hydroxy-3-ethylpentyl and 4-hydroxy-4-methylpentyl.

25. A compound selected from the group consisting of 1α,3β-Dihydroxy-20(R)-(4-hydroxy-4-methylpentylthio)-9,10-secopregna-5,7,10(19)-triene; 1α,3β-Dihydroxy-20(R)-(3-ethyl-3-hydroxypentylthio)-9,10-secopregna-5,7,10(19)-triene; and 20(S)-(3-Ethyl-3-hydroxypentylthio)-1α,3β,16α-trihydroxy-9,10-secopregna-5,7,10(19)-triene.

26. A compound of the general formula (VI):

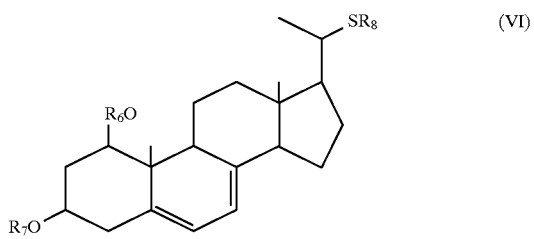

wherein $R_6$ and $R_7$, which may be the same or different, each represents a hydrogen atom or a protective group, and $R_8$ represents a C1-10 alkyl group which may be substituted.

27. A compound according to claim 26 wherein the protective group is an acyl or a substituted silyl group, and $R_8$ is a C1-10 alkyl group substituted by one or more hydroxyl groups.

28. A compound according to claim 27 wherein $R_8$ is a group of the general formula (III):

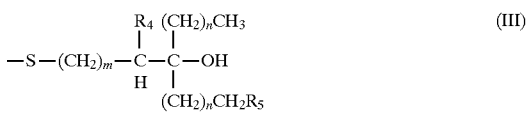

wherein $R_4$ and $R_5$, which may be the same or different, each represents a hydrogen atom or a hydroxyl group provided that the both are not hydroxyl groups, m represents an integer of 1 through 4, and n represents an integer of 0 through 2.

29. A compound according to claim 26 of the general formula (X):

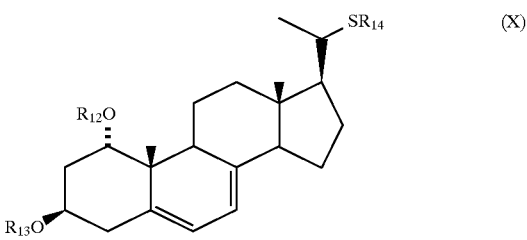

wherein $R_{12}$ and $R_{13}$, which may be the same or different, each represents a hydrogen atom or a protective group, and $R_{14}$ represents a C1-10 alkyl group which may be substituted.

30. A compound according to claim 29 wherein the protective group is an acyl or a substituted silyl group, and $R_{14}$ is a C1-10 alkyl group substituted by one or more hydroxyl groups.

31. A compound of the general formula (XI):

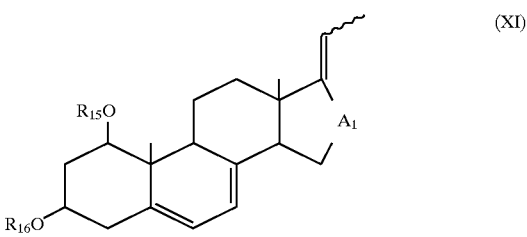

wherein $R_{15}$ and $R_{16}$, which may be same or different, each represents a hydrogen atom or a protective group, and $A_1$ represents —CHOH— or —CO—.

32. A compound according to claim 31 wherein the protective group is a substituted silyl group.

33. A compound according to claim 31 of the general formula (XII):

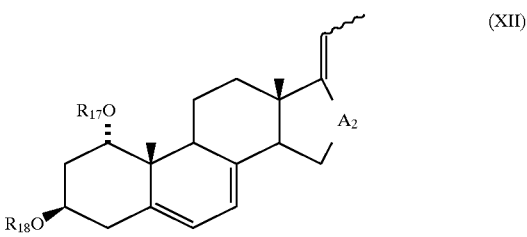

wherein $R_{17}$ and $R_{18}$, which may be the same or different, each represents a hydrogen atom or a protective group, and $A_2$ represents —CHOH— or —CO—.

34. A compound of the general formula (XIII):

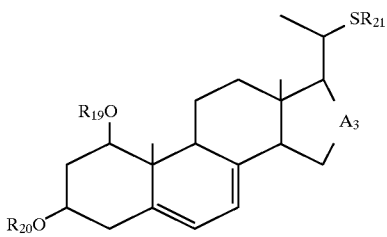

wherein $R_{19}$ and $R_{20}$, which may be the same or different, each represents a hydrogen atom or a protective group, $R_{21}$ represents a C1-10 alkyl group which may be substituted, and $A_3$ represents —CHOH— or —CO—.

35. A compound according to claim 34 wherein the protective group is a substituted silyl group, and $R_{21}$ is a C1-10 alkyl group substituted by one or more hydroxyl groups.

36. A compound according to claim 35 wherein $R_{21}$ is a group of the general formula (III):

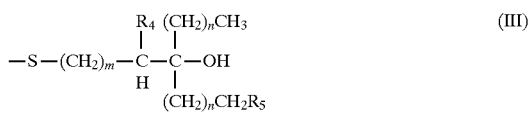

wherein $R_4$ and $R_5$, which may be the same or different, each represents a hydrogen atom or a hydroxyl group provided that the both are not hydroxyl groups, m represents an integer of 1 through 4, and n represents an integer through 0 to 2.

37. A compound according to claim 34 of the general formula (XIV):

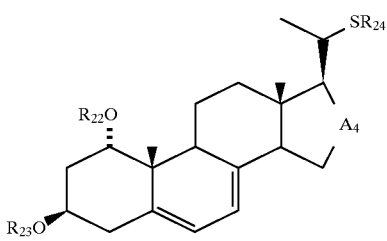

wherein $R_{22}$ and $R_{23}$, which may be the same or different, each represents a hydrogen atom or a protective group, $R_{24}$ represents a C1-10 alkyl group which may be substituted, and $A_4$ represents —CHOH— or —CO—.

38. A process for preparing a compound of the general formula (XVI):

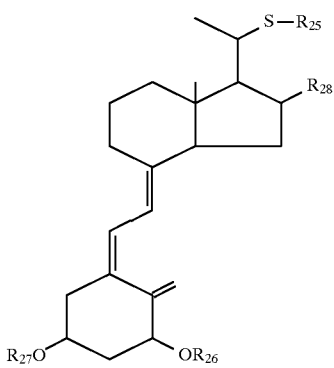

wherein $R_{25}$ represents a C1-10 alkyl group which may be substituted by one or more hydroxyl groups, $R_{26}$ and $R_{27}$, which may be the same or different, each represents a hydrogen atom or a protective group, and $R_{28}$ represents a hydrogen atom or a hydroxyl group, said process comprising the step of subjecting a compound of the general formula (XV):

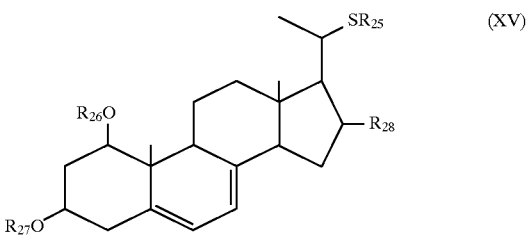

wherein $R_{25}$, $R_{26}$, $R_{27}$ and $R_{28}$ are as defined above, to a light irradiation reaction and a thermal isomerization reaction.

39. A process for preparing a compound of the general formula (VI):

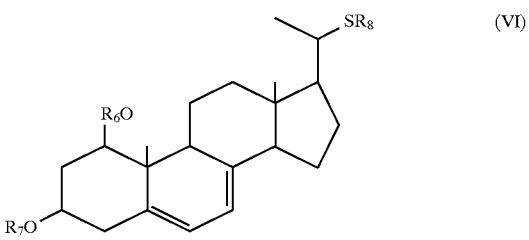

wherein $R_6$ and $R_7$, which may be the same or different, each represents a hydrogen atom or a protective group, and $R_8$ represents a C1-10 alkyl group which may be substituted, said process comprising the step of reacting a compound of the general formula (IV):

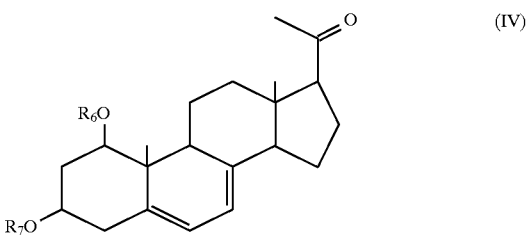

wherein $R_6$ and $R_7$ are as defined above, with a compound of the general formula (V):

wherein $R_8$ is as defined above, under reducing conditions.

40. A process for preparing a compound of the general formula (IX):

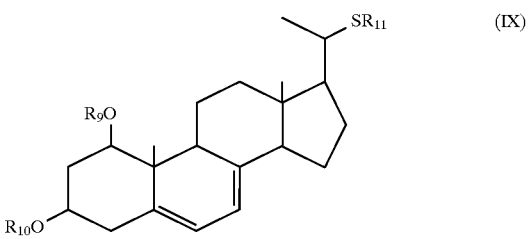

wherein $R_9$ and $R_{10}$, which may be the same or different, each represents a hydrogen atom or a protective group, and $R_{11}$ represents a C1-10 alkyl group which may be substituted, said process comprising the step of reacting a compound of the general formula (VII):

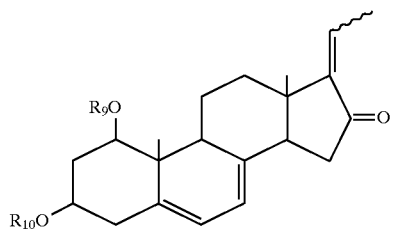
(VII)
wherein $R_9$ and $R_{10}$ are as defined above, with a compound of the general formula (VIII):
$$R_{11}-SH \qquad (VIII)$$
wherein $R_{11}$ is as defined above, under basic conditions.
* * * * *

UNITED STATES PATENT AND TRADEMARK OFFICE
CERTIFICATE OF CORRECTION

PATENT NO.    : 5,824,811
DATED         : October 20, 1998
INVENTOR(S)   : Noboru Kubodera and Akira Kawase It is certified that error appears in the above-identified patent and that said Letters Patent is hereby corrected as shown below:

Column 2,
Lines 53-57, delete formula (III) and insert therefor 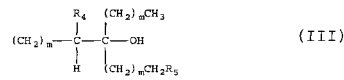

Column 5,
Lines 33-37, delete formula (III) and insert therefor 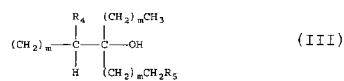

Column 46,
Lines 58-62, delete formula (III) and insert therefor 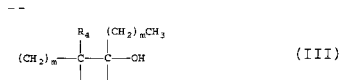

Column 48,
Lines 1-5, delete formula (III) and insert therefor 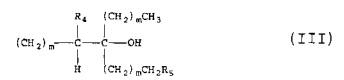

Lines 39-43, delete formula (III) and insert therefor 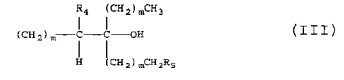

Column 50,
Lines 1-5, delete formula (III) and insert therefor 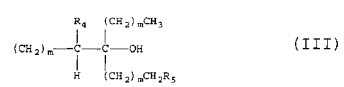

Column 51,
Lines 22-26, delete formula (III) and insert therefor 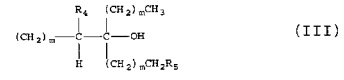

Signed and Sealed this

Twenty-eighth Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 5,824,811
DATED : October 20, 1998
INVENTOR(S) : Noboru Kubodera and Akira Kawase It is certified that error appears in the above-identified patent and that said Letters Patent is hereby corrected as shown below:

Column 46,
Lines 21 and 49, delete "or a secondary carbon atom"

Column 47,
Lines 57-58, delete ", and $R_2$ represents a hydrogen atom or a hydroxyl group"

Column 48,
Line 37, delete "$C_{1-10}$" and insert therefor -- $C_{2-10}$ --

Column 49,
Line 35, after "methylpentyl" and before the period, insert -- provided that when $R_2$ is a hydrogen atom and $R_3$ is a hydroxyl group, the terminal carbon atom of $R_1$ is not a secondary carbon atom --

Column 51,
Lines 53-62, delete formula (IX) and insert therefor
--

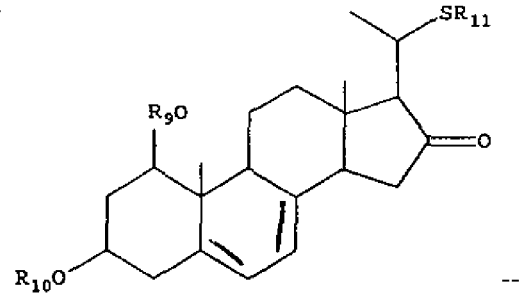

--

Signed and Sealed this

Fifth Day of April, 2005

JON W. DUDAS
*Director of the United States Patent and Trademark Office*